(12) United States Patent
Moskowitz et al.

(10) Patent No.: US 8,353,913 B2
(45) Date of Patent: Jan. 15, 2013

(54) BI-DIRECTIONAL FIXATING TRANSVERTEBRAL BODY SCREWS AND POSTERIOR CERVICAL AND LUMBAR INTERARTICULATING JOINT CALIBRATED STAPLING DEVICES FOR SPINAL FUSION

(76) Inventors: Ahmnon D. Moskowitz, Rockville, MD (US); Mosheh T. Moskowitz, Rockville, MD (US); Nathan C. Moskowitz, Rockville, MD (US); Pablo A Valdivia Y Alvarado, Cambridge, MA (US)

( * ) Notice: Subject to any disclaimer, the term of this patent is extended or adjusted under 35 U.S.C. 154(b) by 0 days.

(21) Appl. No.: 13/084,543

(22) Filed: Apr. 11, 2011

(65) Prior Publication Data
US 2011/0295327 A1    Dec. 1, 2011

Related U.S. Application Data

(63) Continuation of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279.

(60) Provisional application No. 60/670,231, filed on Apr. 12, 2005.

(51) Int. Cl.
*A61B 17/56* (2006.01)
(52) U.S. Cl. .................................... 606/86 A
(58) Field of Classification Search ............... 606/86 A, 606/251, 246, 301, 247, 250, 252, 99, 248, 606/279; 623/17.11, 17.15, 17.16
See application file for complete search history.

(56) References Cited

U.S. PATENT DOCUMENTS

| 4,554,914 A | 11/1985 | Kapp et al. |
| 4,636,217 A | 1/1987 | Ogilvie et al. |
| 4,904,261 A | 2/1990 | Dove et al. |
| 4,960,420 A | 10/1990 | Goble et al. |
| 4,997,432 A | 3/1991 | Keller |
| 5,123,926 A | 6/1992 | Pisharodi |
| 5,290,312 A | 3/1994 | Kojimoto et al. |
| 5,514,180 A | 5/1996 | Heggeness et al. |
| 5,660,188 A | 8/1997 | Groiso |

(Continued)

OTHER PUBLICATIONS

International Search Report (ISR) and Written Opinion of the International Searching Authority, Jul. 9, 2008, International Application No. PCT/US07/021013.

(Continued)

*Primary Examiner* — Pedro Philogene
(74) *Attorney, Agent, or Firm* — Dresch IP Law, PLLC; John J. Dresch

(57) ABSTRACT

A self-drilling bone fusion screw apparatus is disclosed which includes at least first and second sliding boxes. A first screw member having a tapered end and a threaded body is disposed within the first sliding box, and a second screw member having a tapered end and a threaded body disposed within the second sliding box. An adjuster adjusts the height of the sliding boxes. The screw members are screwed into vertebral bodies in order to fuse the vertebral bodies together. A plurality of the self-drilling bone fusion screw apparatuses may be attached together and/or integrated via a plate or cage. Also disclosed is a cervical facet staple that includes a curved staple base and at least two prongs attached to the bottom surface of the curved staple base.

44 Claims, 41 Drawing Sheets

U.S. PATENT DOCUMENTS

| | | | |
|---|---|---|---|
| 5,667,472 | A | 9/1997 | Finn et al. |
| 5,782,832 | A | 7/1998 | Larsen et al. |
| 5,960,522 | A | 10/1999 | Boe |
| 6,126,689 | A | 10/2000 | Brett |
| 6,368,350 | B1 | 4/2002 | Erickson et al. |
| 6,375,682 | B1 | 4/2002 | Fleischmann et al. |
| 6,419,704 | B1 | 7/2002 | Ferree |
| 6,458,159 | B1 | 10/2002 | Thalgott |
| 6,527,804 | B1 | 3/2003 | Gauchet et al. |
| 6,533,818 | B1 | 3/2003 | Weber et al. |
| 6,572,653 | B1 | 6/2003 | Simonson |
| 6,579,318 | B2 | 6/2003 | Varga et al. |
| 6,582,468 | B1 | 6/2003 | Gauchet |
| 6,641,614 | B1 | 11/2003 | Wagner et al. |
| 6,655,243 | B2 * | 12/2003 | Anderson et al. ............... 81/490 |
| 6,719,794 | B2 | 4/2004 | Gerber |
| 6,723,126 | B1 | 4/2004 | Berry |
| 6,733,532 | B1 | 5/2004 | Gauchet et al. |
| 6,764,491 | B2 | 7/2004 | Frey et al. |
| 6,770,094 | B2 | 8/2004 | Fehling et al. |
| 6,904,308 | B2 | 6/2005 | Frisch et al. |
| 6,955,671 | B2 | 10/2005 | Uchikubo |
| 6,972,019 | B2 * | 12/2005 | Michelson ................ 606/86 A |
| 7,030,904 | B2 | 4/2006 | Adair et al. |
| 7,037,258 | B2 | 5/2006 | Chatenever et al. |
| 7,077,864 | B2 * | 7/2006 | Byrd et al. ................. 623/17.11 |
| 7,097,615 | B2 | 8/2006 | Banik et al. |
| 7,232,464 | B2 | 6/2007 | Mathieu et al. |
| 7,238,203 | B2 * | 7/2007 | Bagga et al. ............. 623/17.11 |
| 7,442,209 | B2 * | 10/2008 | Michelson ................ 623/17.11 |
| 7,618,456 | B2 * | 11/2009 | Mathieu et al. ........... 623/17.11 |
| 7,846,207 | B2 | 12/2010 | Lechmann et al. |
| 7,862,616 | B2 * | 1/2011 | Lechmann et al. ........ 623/17.11 |
| 7,875,076 | B2 | 1/2011 | Mathieu et al. |
| 7,887,591 | B2 * | 2/2011 | Aebi et al. ................. 623/17.15 |
| 7,959,675 | B2 * | 6/2011 | Gately ....................... 623/17.11 |
| 2002/0068977 | A1 | 6/2002 | Jackson |
| 2004/0088054 | A1 | 5/2004 | Berry |
| 2004/0177531 | A1 | 9/2004 | DiBenedetto et al. |
| 2004/0254644 | A1 | 12/2004 | Taylor |
| 2005/0027362 | A1 | 2/2005 | Williams et al. |
| 2005/0049590 | A1 | 3/2005 | Alleyne et al. |
| 2005/0177235 | A1 | 8/2005 | Baynham et al. |
| 2005/0216084 | A1 | 9/2005 | Fleischmann |
| 2005/0273170 | A1 | 12/2005 | Navarro et al. |
| 2005/0278026 | A1 | 12/2005 | Gordon et al. |
| 2010/0305704 | A1 | 12/2010 | Messerli et al. |

OTHER PUBLICATIONS

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.

E.K. Wai et al., "Disk Replacement Arthroplasties: Can the Success of Hip and Knee Replacements be Repeated in the Spine?," Seminars in Spine Surgery, vol. 15, No. 4 (Dec.) 2003, pp. 473-482.

Richard D. Guyer et al., "Intervertebral Disc Prostheses," Spine Journal, vol. 28, No. 15S, Supp. to Aug. 1, 2003, pp. S15-S23.

Dieter Grob et al., "Clinical Experience With the Dynesys Semirigid Fixation System for the Lumbar Spine," Spine, vol. 30, No. 3, 2005, pp. 324-331.

International Search Report (ISR) and Written Opinion of the International Searching Authority, Dec. 3, 2007, International Application No. PCT/US 07/05005.

* cited by examiner

BI-DIRECTIONAL FIXATING TRANSVERTEBRAL BODY SCREWS AND POSTERIOR CERVICAL AND LUMBAR INTERARTICULATING JOINT CALIBRATED STAPLING DEVICES FOR SPINAL FUSION

CROSS-REFERENCE TO RELATED APPLICATIONS

This application is a Continuation Application of application Ser. No. 11/842,855, filed on Aug. 21, 2007, now U.S. Pat. No. 7,942,903 issued on May 17, 2011, which is a Continuation-In-Part Application of application Ser. No. 11/536,815, filed on Sep. 29, 2006, now U.S. Pat. No. 7,846,188 issued on Dec. 7, 2010, which is a Continuation-In-Part Application of application Ser. No. 11/208,644, filed on Aug. 23, 2005, now U.S. Pat. No. 7,704,279 issued on Apr. 27, 2010, for which priority is claimed under 35 U.S.C. §120; and this application also claims priority under 35 U.S.C. §119(e) of U.S. provisional application No. 60/670,231, filed on Apr. 12, 2005; the entire contents of all the above identified patent applications are hereby incorporated by reference.

BACKGROUND OF THE INVENTION

1. Field of Invention

The present invention relates to a unique universal bidirectional screw (BDS) system, and in particular its application to the spine, also referred to as bi-directional fixating transvertebral (BDFT) screws which can be used as a stand-alone intervertebral device which combines the dual functions of an intervertebral spacer which can be filled with bone fusion material(s), as well as a transvertebral bone fusion screw apparatus. In the posterior lumbosacral and thoracic spine, BDFT screw/box constructs can be used independently or supplemented with a novel horizontal mini-plate which prevents upward bone graft intrusion into the thecal sac and nerves. In the anterior lumbosacral spine BDFT screw box constructs can be inserted into and supplemented by a circumferential cage. These posteriorly and anteriorly placed stand-alone intervertebral body fusion constructs may obviate the need for supplemental pedicle screw fixation.

The present invention also relates to stand-alone or supplemental posterior cervical and lumbar calibrated inter-articular joint stapling devices which may obviate and/or lessen the need for supplemental pedicle screw fixation.

2. Description of the Relevant Art

The history and evolution of instrumented spinal fusion in the entire human spine has been reviewed in our two prior copending applications Ser. No. 11/536,815, filed on Sep. 29, 2006, and Ser. No. 11/208,644, filed on Aug. 23, 2005, the related contents of which are hereby incorporated by reference. Currently the majority of posterior cervical and almost all anterior and posterior lumbosacral and thoracic fusion techniques are typically supplemented with pedicle screw placement. Complications of pedicle screw placement in cervical, thoracic and lumbar spine include duration of procedure, significant tissue dissection and muscle retraction, misplaced screws with neural and/or vascular injury, excessive blood loss, need for transfusions, prolonged recovery, incomplete return to work, and excess rigidity leading to adjacent segmental disease requiring further fusions and re-operations. Recent advances in pedicle screw fixation including minimally invasive and image-guided technology, and the development of flexible rods, imperfectly address some but not all of these issues.

Complications of all current spinal interbody fusion devices is their lack of coverage of the majority of the cross-sectional area of the vertebral endplates, and their lack of adequate, if any capacity to penetrate bone, and hence the heightened risk of implant extrusion. Furthermore the bone and biological bone fusion agents which are packed into the intervertebral space can easily blossom and grow upward into the thecal sac causing neural compression, in the absence of a physical barrier between the fusing growing bone, and the thecal sac.

SUMMARY

Herein we describe multiple device embodiments which combine in a single construct the dual functions of an intervertebral spacer maintaining disc space height, and transvertebral body fusion screws.

We also introduce an entirely novel horizontal mini-plate capping off the intervertebral space capable of functioning as a physical barrier preventing upward bone intrusion and/or compression of the ventral thecal sac, and traversing and exciting nerve roots.

Furthermore, we present an advanced mechanism in calibrated posterior facet joint stapling compared to our previous designs illustrated in our co-pending patents. We also introduce the entirely novel concept of posterior cervical facet staples to obviate and/or diminish the need for posterior cervical pedicle screw instrumented fusion. Using combinations and permutations of different embodiments of cervical facet staples in a modular manner advances the concept of flexible fusion in the cervical spine.

To achieve safe, effective and minimally invasive segmental spinal fusion, applicants propose the use of novel bi-directional fixating transvertebral (BDFT) screws which can be strategically inserted via anterior or posterior surgical spinal approaches into the anterior and middle columns of the interverterbral disc space. In our previous applications these bi-directional screws employed turning a wormed driving screw which turns a spur gear which in turn simultaneously turns a rostral oriented screw into the cephalad vertebral body, and a caudal directed screw into the caudal vertebral body. The vertebral bodies above and below the disc space by virtue of their engagement and penetration by the BDFT screws are thus linked, interlocked, and eventually biologically fused with placement of intervertebral bone agents.

In this current application one or more of the described embodiments may eliminate the intervening wormed driving screws and gears required by previous designs, e.g., a gearless screw box is achieved. We have designed a screw box to be placed inter-vertebrally, either unilaterally or bilaterally, in particular, posteriorly between vertebral bodies. The housing screw box incorporates built-in screw and/or drill guides which allow the direct placement and insertion of two self drilling screws which are driven in two opposing directions into superior and inferior vertebral bodies, respectively. One screw within the screw box is angled superiorly, and the other screw in the screw box is angled inferiorly.

In yet another embodiment, in addition to these features we designed an expanding screw box with sliding triangular bases to house two screws driven in two opposing directions which can be expanded in two simultaneous directions, height and depth, by turning a built-in screw adjuster. This is accomplished by a combined positioning tool/screw guide/cage expander to further enhance trajectory precision and to simultaneously expand the screw box in height and depth to custom-fit the individual disc space height. This embodiment has two sub-embodiments; one has two laterally oriented BDFT screws, and the other has a lateral and a medial oriented BDFT screw. These innovations represent a continued evolution of our concept of expandable fusion cages described in our previous co-pending patents.

In yet another embodiment we designed a screw box which houses only one, instead of two screws. Each box allows the placement of one superior or inferior directed screw on one side (left or right), and the contra lateral screw box device allows placement of an inferior or superior oriented screw which goes in the opposite direction of the contra lateral device. In totality these two separate single screw boxes fuse the superior and inferior vertebrae. The potential advantage of this embodiment is that it diminishes the width of the screw box in cases where it might be favorable to have less nerve root retraction with a smaller width device.

In all screw-box embodiments, a rostral-directed screw is passed through one built-in screw guide of the device which then is inserted and screwed into the superior vertebral body. Then a caudaly directed screw is passed through an adjacent built-in screw guide which then is inserted and screwed into the inferior vertebral body. The novelty of this design is the built-in prescribed angles of the integral screw guides which allow the posterior transvertebral penetration into the vertebral bodies. This is a truly amazing feat accomplished in the posterior lumbar spine considering the small anatomically restricted work zone within which to work, which is very narrowly prescribed by obtuse angulations between screw and intervertebral bone surfaces, and by nerve root, facet joint and pedicle. We have also designed a positioning tool for the placement of the non-expandable screw boxes which has a screwdriver with a flexible shaft specifically designed to fit these devices if a straight screw driver impedes screw placement. Hence these external tools provide the means in any circumstance to accomplish precision screw trajectory. The embodiments described herein compared to our previous co-pending patent designs, streamline and ease production of bi-directionally oriented transvertebral screws, and allows placement of longer and wider screws with greater bone penetration to provide yet a sturdier fusion construct. The designs are also easily modifiable for anterior placement into the cervical spine. The expandable embodiment of the screw box can also be enlarged and modified to be suitable for cervical, thoracic and lumber vertebral body replacements.

The box casings have multiple perforations to allow both screw traversal and horizontal bone packing preventing upward vertical migration of bone. The boxes prevent subsidence. Both the inside of the denuded intervertebral space, and the screw boxes can be packed with autologous or allograft bone, BMP, DBX or similar osteoconductive material. Posteriorly or anteriorly in the lumbar spine, these screws can be capped with a horizontal mini-plate which will prevent bony growth into the thecal sac and nerves. We refer to this as a two-in-one device, i.e. two screw boxes/BDFT screws combined with one horizontal mini-plate. This is an entirely novel concept in posterior lumbar spinal surgery. In yet another embodiment two BDFT screw boxes can be combined with a circumferential cage (also 2 in 1) to be placed anteriorly into the lumbar spine.

It is believed that BDFT-screw constructs provide as strong or stronger segmental fusion as pedicle screws without the complications arising from pedicle screw placement which include screw misplacement with potential nerve and/or vascular injury, violation of healthy facets, possible pedicle destruction, blood loss, and overly rigid fusions. By placing screws across the intervertebral space from vertebral body to vertebral body, engaging anterior and middle spinal columns, and not the vertebral bodies via the transpediclar route, the healthy facet joints, if they exist, are preserved. Because this technique accomplishes both anterior and middle column fusion, without rigidly fixating the posterior column, it in essence creates a flexible fusion. This device therefore is a flexible fusion device because the preserved posterior facet joints retain their function achieving at least a modicum of mobility and hence a less rigid (i.e. a flexible) fusion.

The very advantage of transpedicular screws which facilitate a strong solid fusion by rigidly engaging all three spinal columns is the same mechanical mechanism whereby complete inflexibility of all columns is incurred thereby leading to increasing rostral and caudal segmental stress which leads to an increased rate of re-operation.

Transvertebral fusion also leads to far less muscle retraction, blood loss, and significant reduction in O.R. time. Thus the complication of pedicular screw pull-out and hence high re-operation rate associated with the current embodiment of flexible fusion pedicle screws/rods is obviated. The lumbosacral screw box embodiments and BDFT screws can be introduced via posterior lateral, transforaminal or anterior interbody fusion approaches/techniques. Although one can opt to supplement these screws with transpedicular screws there would be no absolute need for supplemental pedicle screw fixation with these operative techniques.

BDFT screw constructs outlined here can also be combined with novel zero-profile horizontal cervical and, lumbar/thoracic mini-plates. Likewise one or two of these devices can be inserted anteriorly with or without circumferential cage supplementation.

Because the BDFT screws engage a small percentage of the rostral and caudal vertebral body surface area, multi-level fusions can be performed with these devices.

Previous improvements included a novel calibrated lumbar/thoracic facet stapling device which staples the inferior articulating facet of the superior segment to the superior articulating facet of the caudal vertebral segment unilaterally or bilaterally, which may minimize motion until interbody fusion occurs. In the present patent application we introduce a new design of the staple enhancing its calibrating capability.

In this patent application we also introduce a novel posterior cervical facet stapling device which staples the inferior articulating facet of the superior cervical segment with the superior articulating facet of the caudal vertebral segment unilaterally or bilaterally.

The advantage of cervical facet staples is speed and safety. The risks of cervical facet pedicle screw fixation which include nerve root and vertebral artery injuries are completely obviated. Thus they thereby achieve the same function of pedicle screws without the risks.

Placement of different embodiments of the cervical facet staples along unilateral and/or bilateral facet joints in a modular manner, lead to differing degrees of calibrated motion joint motion hence introducing for the first time the concept of calibrated cervical fusion.

Currently failed anterior lumbar arthroplasties are salvaged by combined anterior and posterior fusions. BDFT screw constructs could be utilized as a one-step salvage operation for failed/extruded anteriorly placed lumbar artificial discs obviating the above salvage procedure which has far greater morbidity.

For example, in one general aspect, a self-drilling bone fusion screw apparatus includes a first sliding box, a second sliding box, positioned relative to the first sliding box, a first screw member having a tapered end and a threaded body disposed within the first sliding box, a second screw member having a tapered end and a threaded body disposed within the second sliding box, and an adjuster for adjusting the height of the sliding boxes.

Implementations of this aspect may include one or more of the following features. For example, the first and second screw members may be medially aligned. At least one of the first and second screw members may be laterally aligned. The first and second screw members are laterally aligned. One of the first and second screw members is laterally aligned and the other screw member is laterally aligned. The first and second sliding boxes may be substantially triangularly shaped. The triangularly shaped first and second sliding boxes may include a sliding rail and ridged surfaces. The triangularly shaped first and second sliding boxes may include holes for bone grafts. The adjuster may include a screw.

In another general aspect, a self-drilling bone fusion screw apparatus includes a box, a first screw member having a tapered end and a threaded body disposed at least partially within the box and laterally aligned with the box, a second screw member having a tapered end and a threaded body disposed at least partially within the box and laterally aligned with the box, and a plurality of ridges disposed on along the sides of the box.

Implementations of this aspect may include one or more of the following features. For example, the apparatus may include bone graft holes. The apparatus may be attachable to a second self-drilling fusion screw apparatus via a plate.

In another general aspect, a self-drilling bone fusion screw apparatus may include a first box, a first screw member having a tapered end and a threaded body disposed at least partially within the first box and laterally aligned with the first box, a second box, a second screw member having a tapered end and a threaded body disposed at least partially within the second box and laterally aligned with the second box, and an attachment member for engaging the first and second boxes.

Implementations of this aspect may include one or more of the following features. For example, the self-drilling bone fusion screw apparatus may include bone graft holes. The plate may be directly joined to the first and second boxes by a plurality of screws. The attachment member for engaging the first and second boxes may include a plate or the attachment member may include a circumferential cage defining at least one recess. The first and the second boxes may be positioned within or securely held within the recess of the circumferential cage, e.g., with an interference fit.

In another general aspect, a tool assembly for manipulating a self-drilling bone fusion screw apparatus includes a handle, a gripper cooperating with the handle and having a plurality of prongs, a screw guide, held in place the plurality of prongs, for controlling the direction of self-drilling screws that are screwed into a vertebral body.

Implementations of this aspect may include one or more of the following features. For example, the tool assembly for manipulating a self-drilling bone fusion screw apparatus may include a key for controlling an adjustment device which controls the height of the self-drilling bone fusion screw apparatus. The tool assembly according to claim may include a driver assembly. The driver assembly may include a handle, a drive bit portion, and a flexible drive shaft extending between the handle and the drive bit portion for manipulating a screw of an expandable or non-expandable screw box. The assembly may include one or more of an expandable screw box and/or a non-expandable screw box. The boxes may include one or more screws. The screw boxes may be joined by or include an attachment member, such as a plate and/or a circumferential cage.

In another general aspect, a cervical facet staple includes a curved staple base, at least two prongs attached to the bottom surface of the curved staple base, and an insertion member disposed on the top surface of the curved staple base.

Implementations of this aspect may include one or more of the following features. For example, the staple may include at least four prongs attached to the bottom surface of the curved staple base. The insertion member may include a threaded insert.

In another general aspect, an impaction tool for a cervical facet staple includes a handle, a stem attached to the handle, a plurality of wings for contacting the cervical facet staple, and an insertion member for coupling the cervical facet staple to the impaction tool.

Implementations of this aspect may include one or more of the following features. For example, the handle may include a flattened portion that can be struck by a mallet.

In another general aspect, a lumbar facet staple includes a pair of rotating arms, at least two prongs attached to the inner surfaces of the rotating arms, a plurality of spurs attached to one of the rotating arms, and a ratchet attached to one of the rotating arms. The rotating arms and prongs are rotated to a closed position to staple a lumbar facet joint.

FIGS. E-G illustrate the sequential steps (I-III) of the positioning tool/screw guide/box expander assembly. Step I (FIG. 5E), step II (FIG. 5F), and step III (FIG. 5G).

Figure 5A:
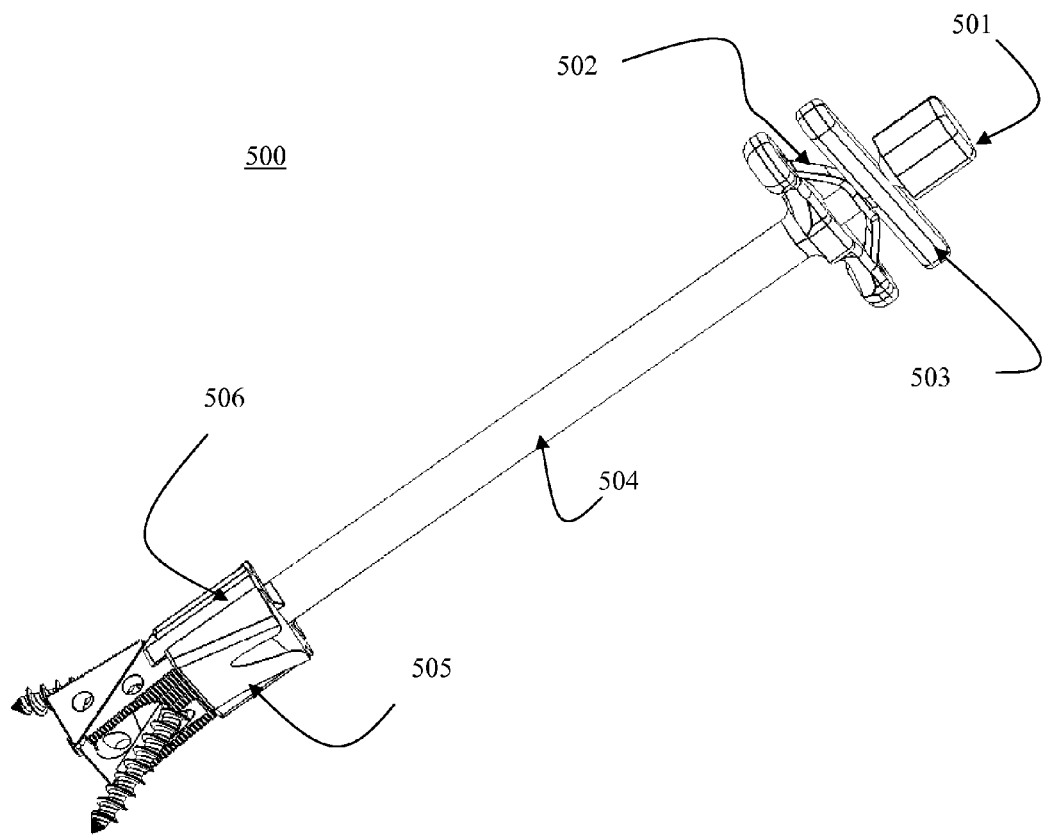
FIGS. 5A-C illustrate t positioning tool/screw guide/box expander in oblique perspective (FIG. 5A), lateral (FIG. 5B), and exploded (FIG. 5C) views.
Figure 5B:
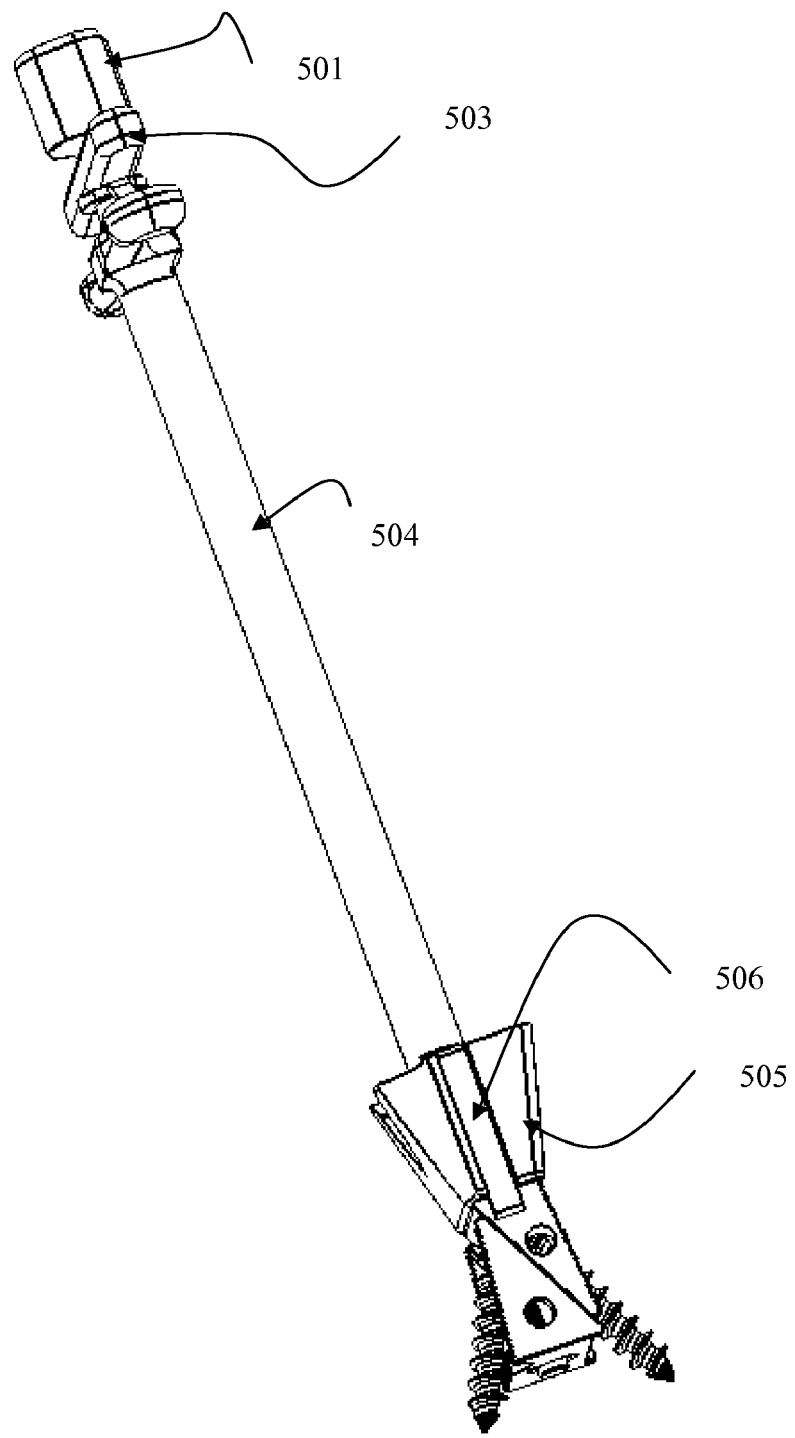
Figure 5C:
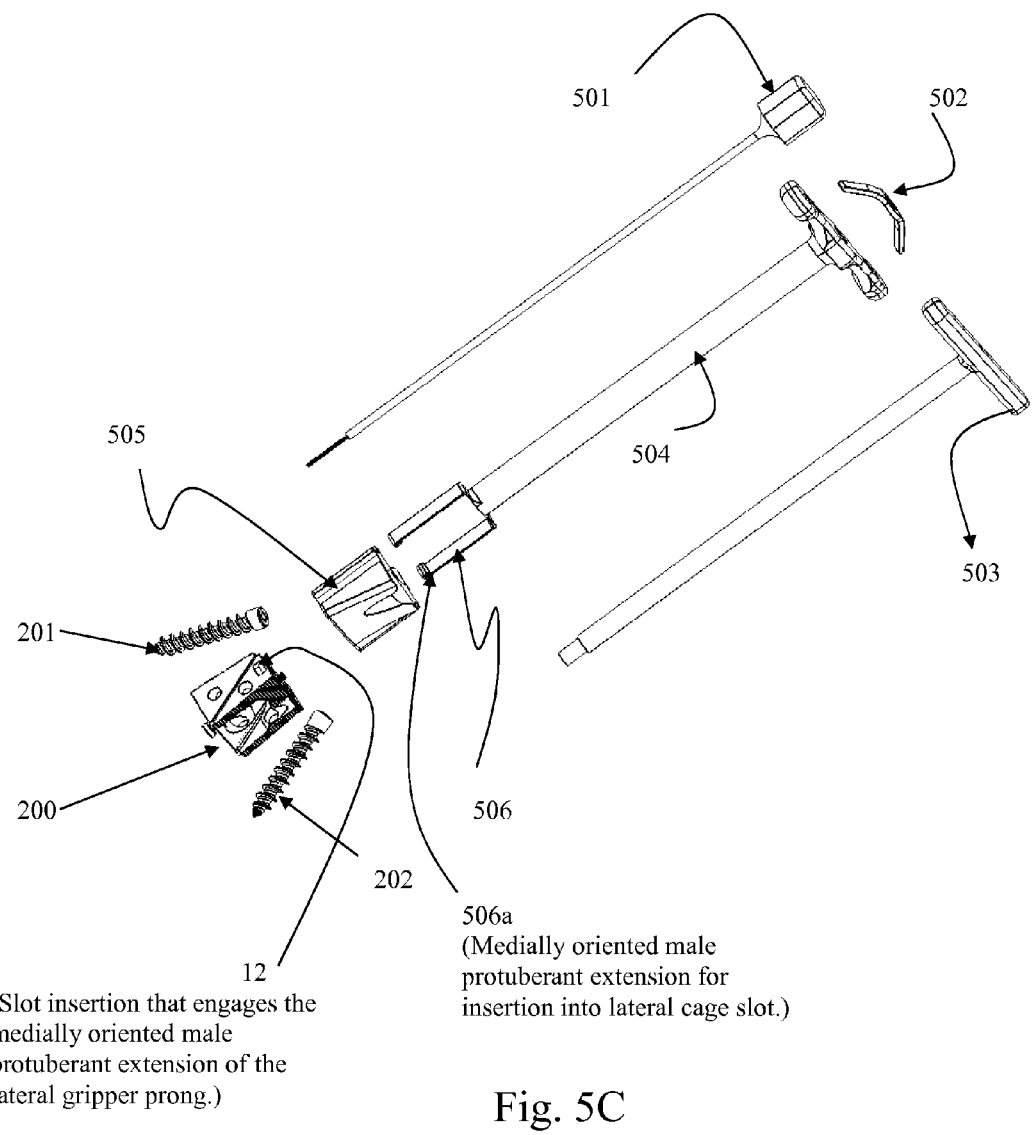
Figure 5D:
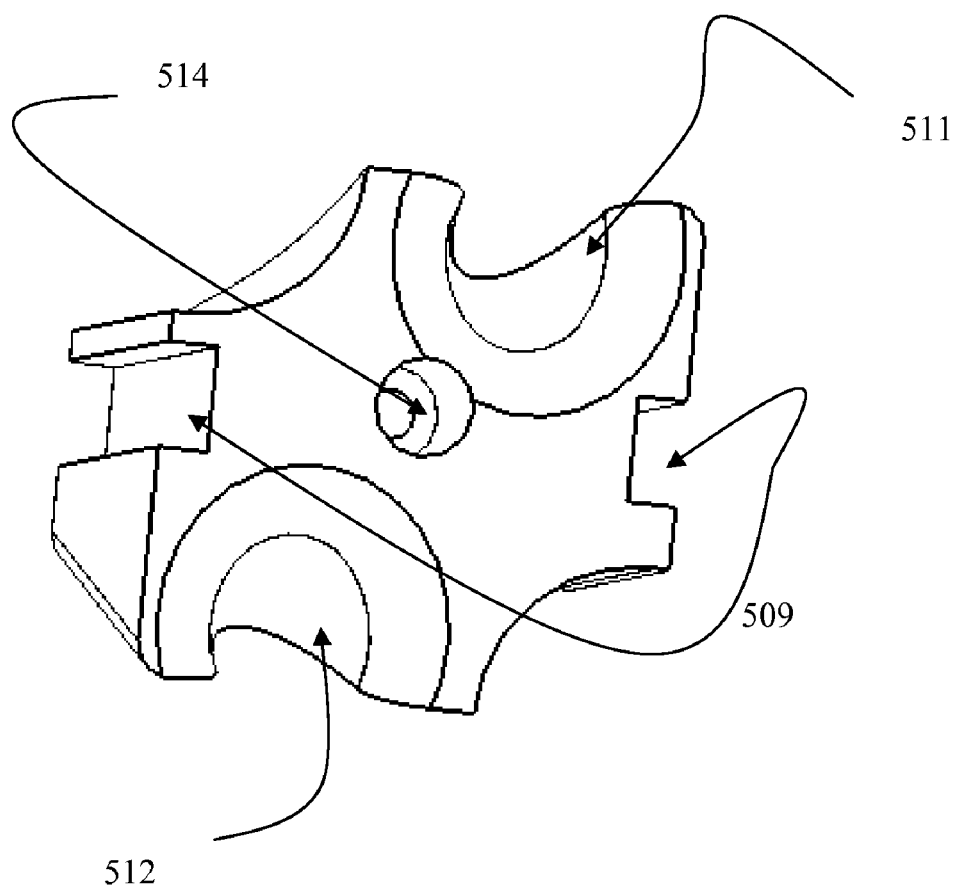
FIG. 5D illustrates a superior oblique perspective view of the positioning tool/drill guide/box expander component.
Figure 5E:
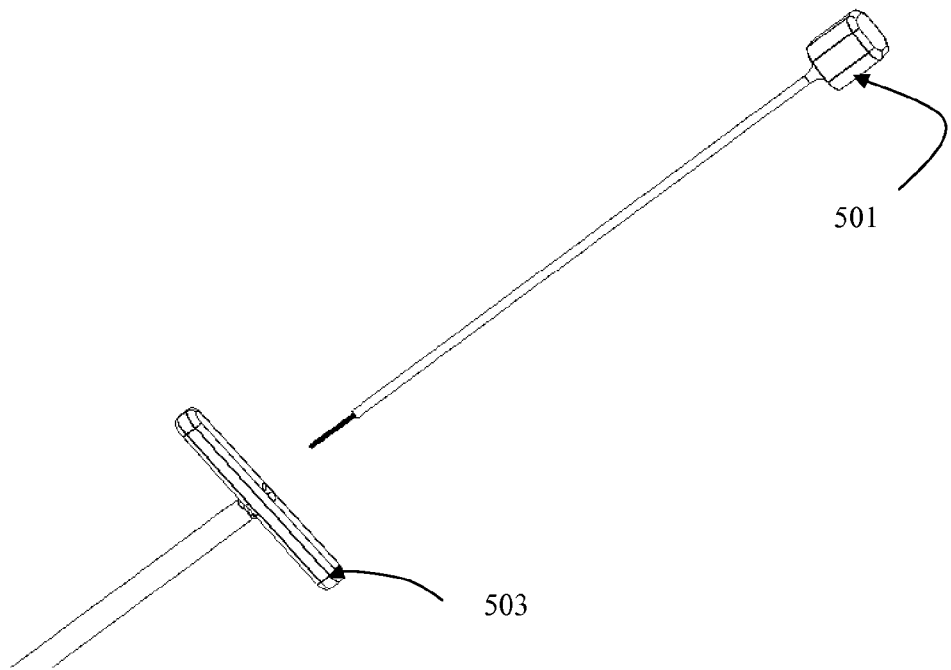
Figure 5F:
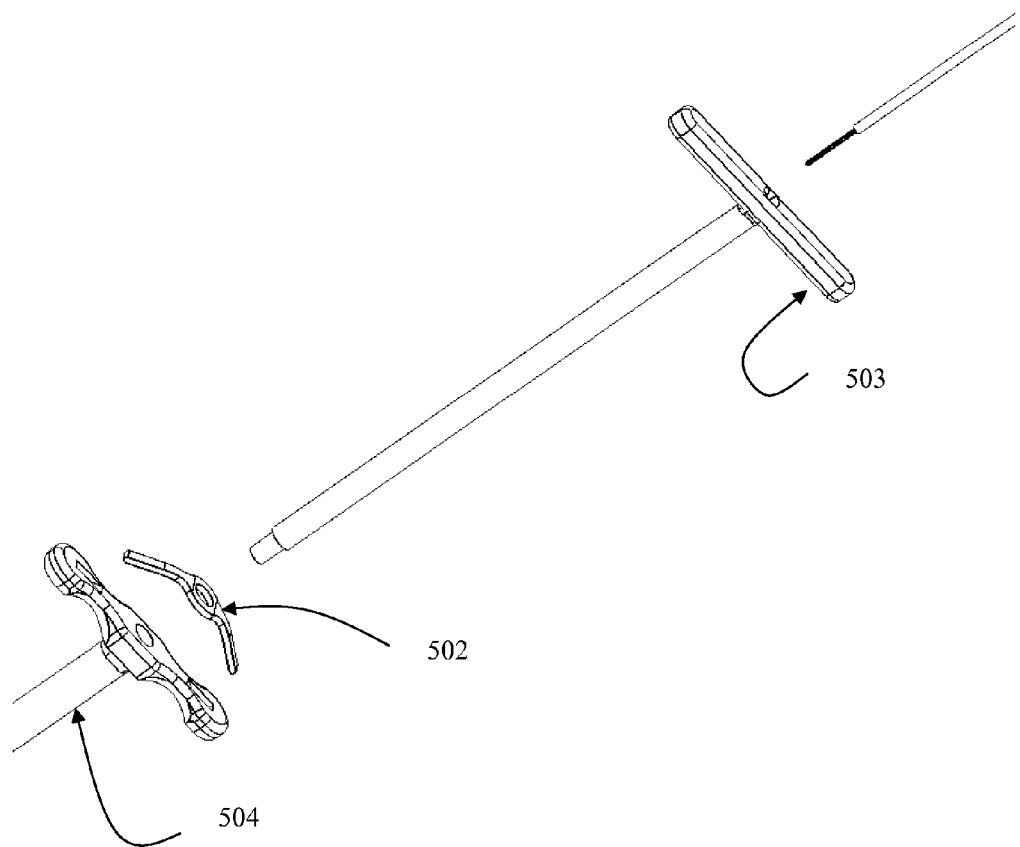
Figure 5G:
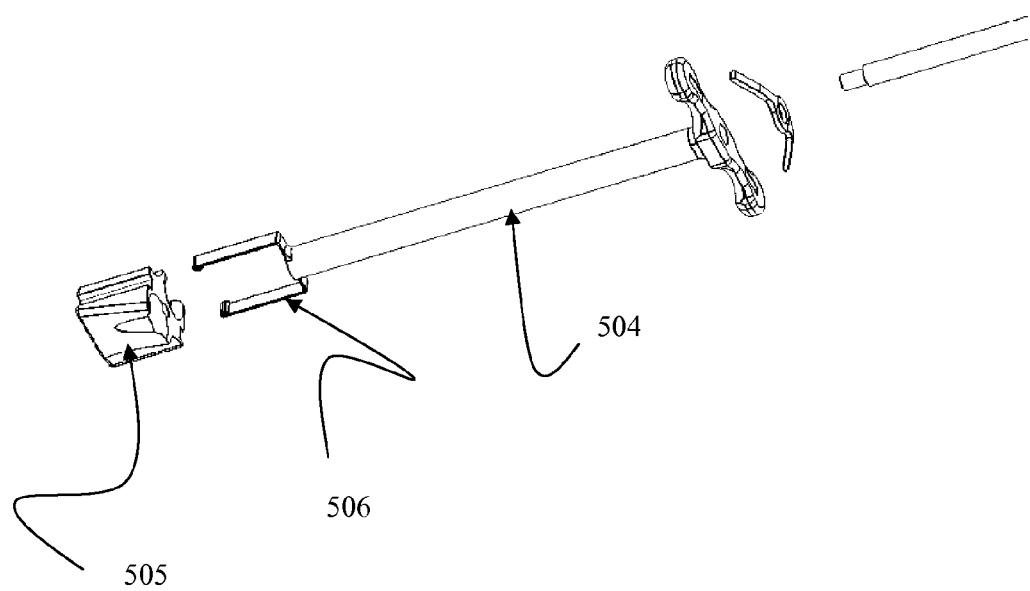
Figure 5H:
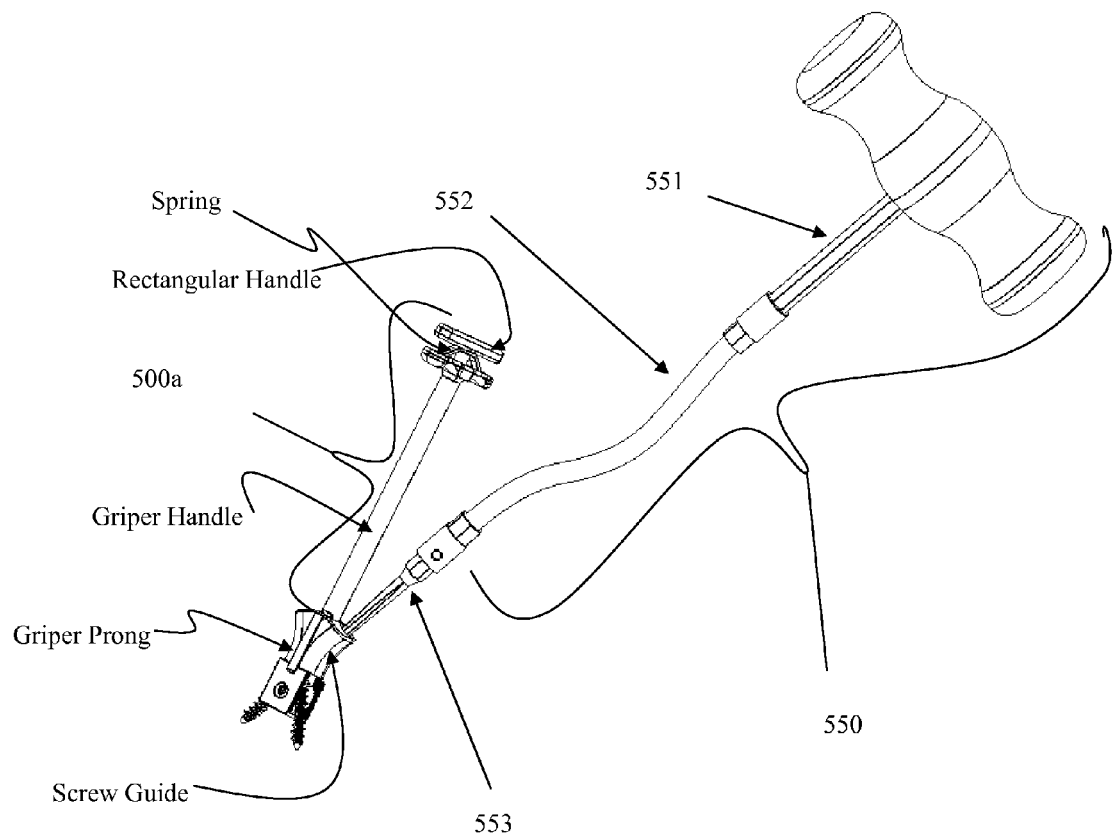
Figure 5I:
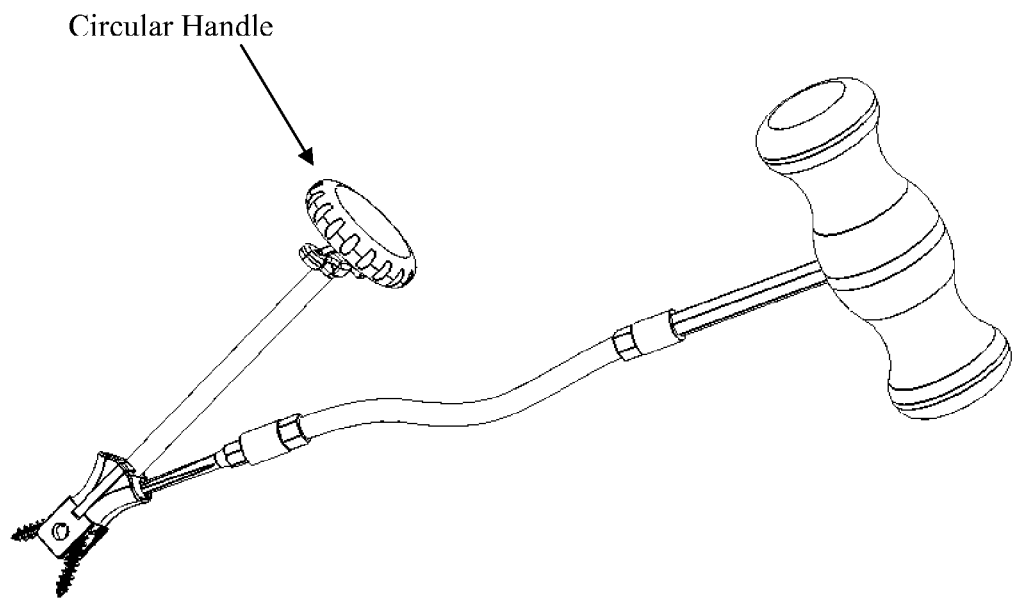

FIGS. 5H-I illustrate the positioning tool for impaction and placement of the non-expandable screw box with two transvertebral screws. Embodiment I has a rectangular positioning handle (FIG. 5H), and embodiment II has a circular positioning handle (FIG. 5I)

Figure 5J:
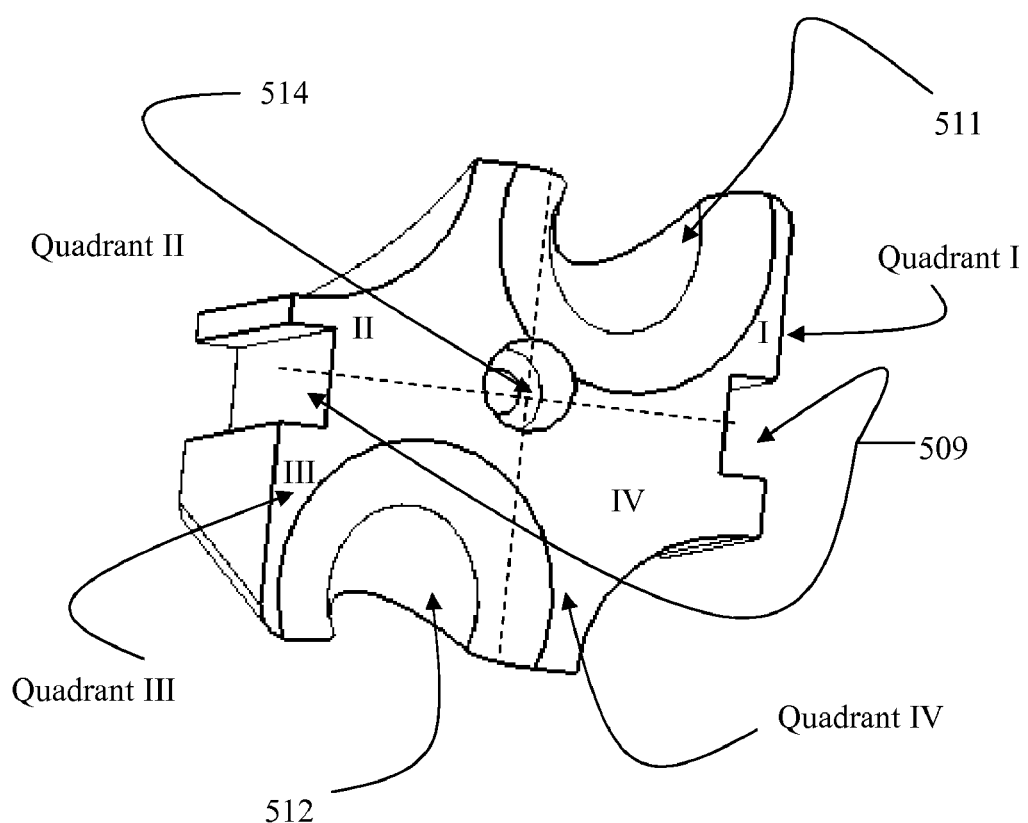

FIG. 5J illustrates another superior oblique perspective view of the positioning tool/drill guide/box expander component with gridlines.

Figure 6A:
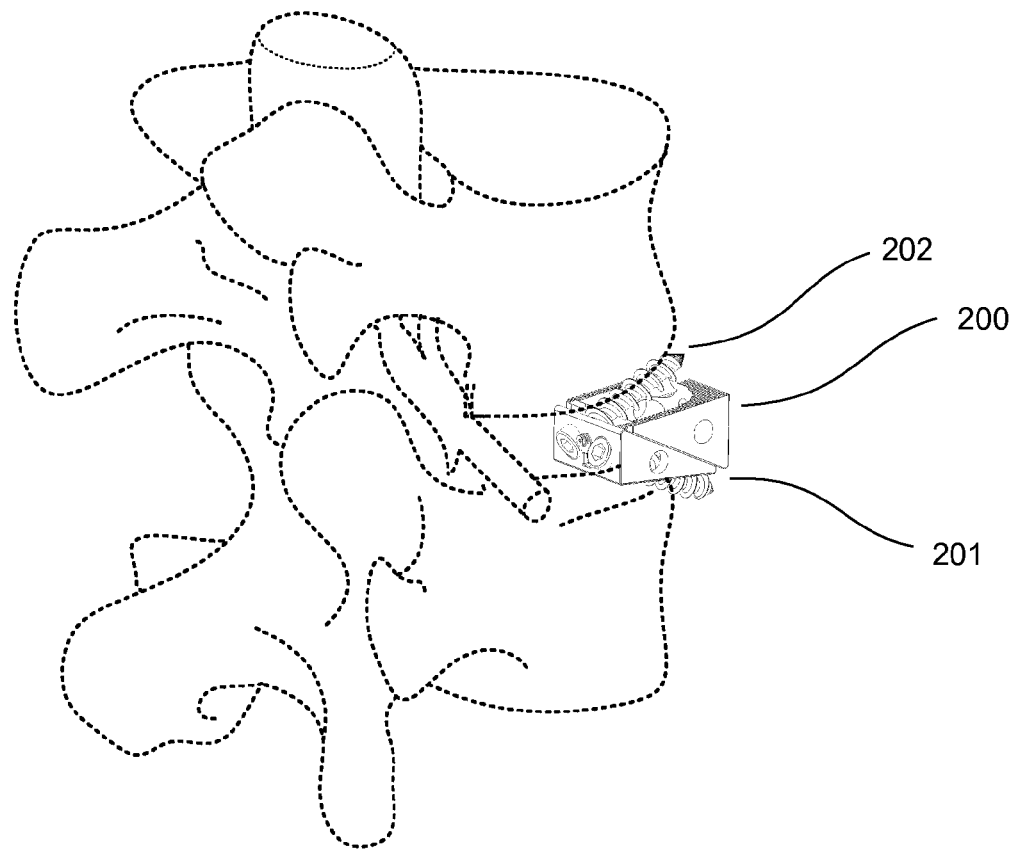
Figure 6B:
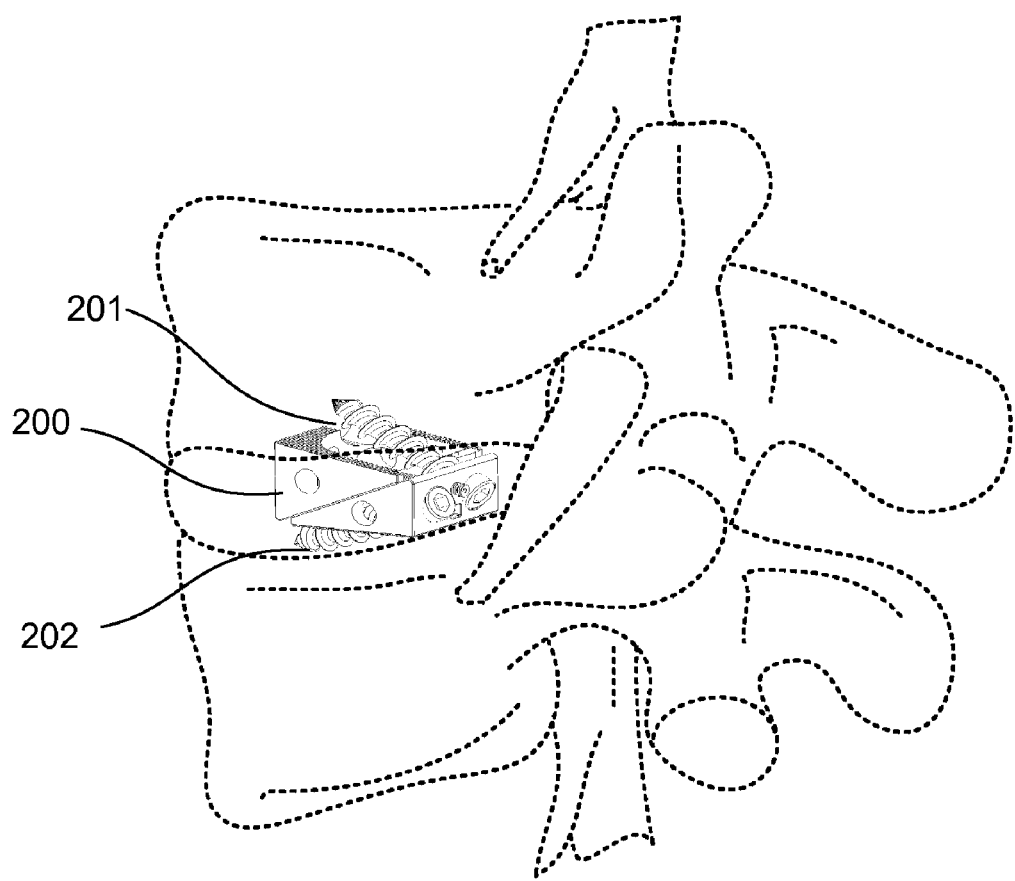

FIGS. 6A-B illustrate the insertion of expandable Lumbar bi-directional screw box with two BDFT screws into the Lumbar spine in oblique (FIG. 6A) and lateral (FIG. 6B) views.

Figure 7A:
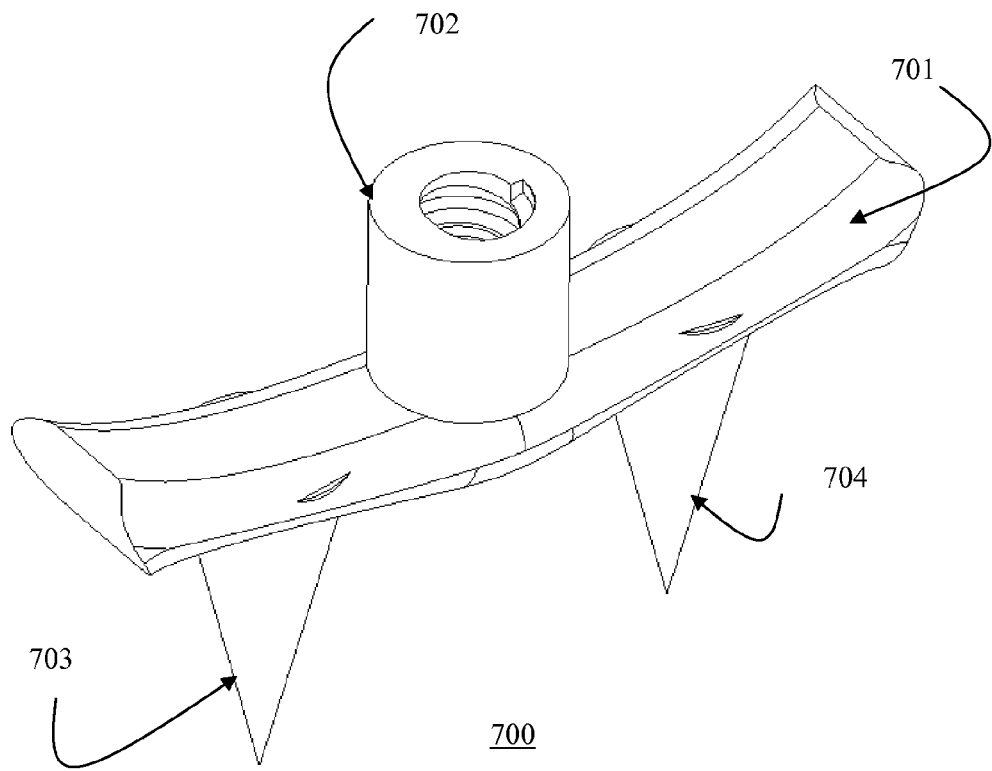
Figure 7B:
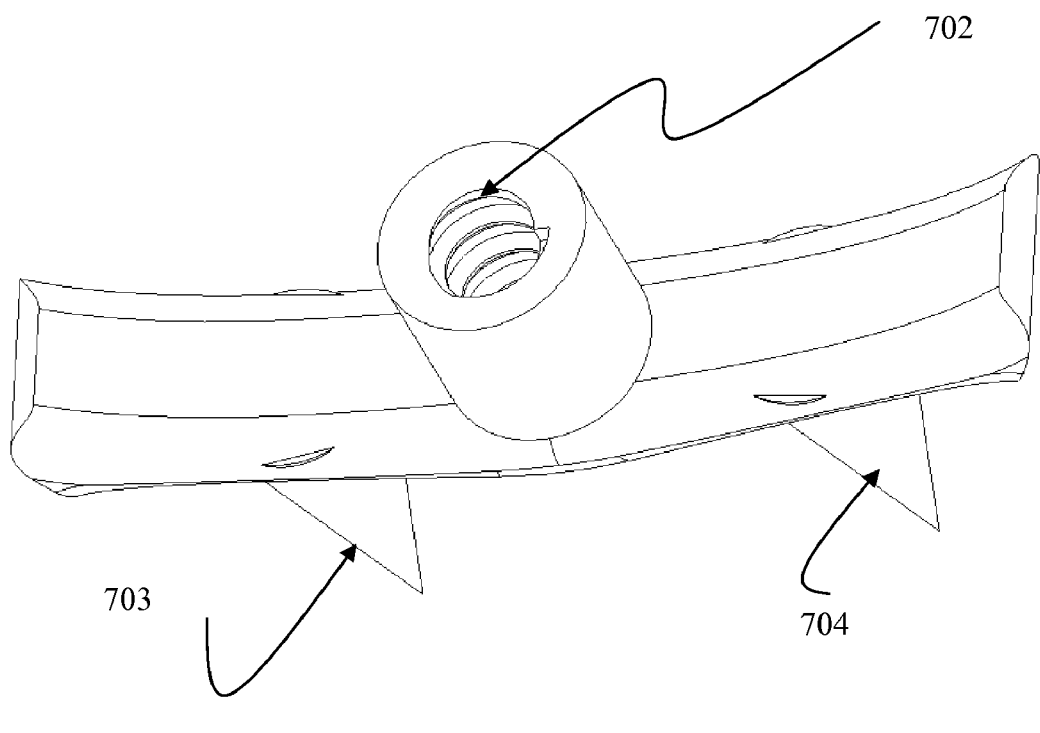

FIGS. 7A-B illustrate the cervical facet staple (Embodiment I) in lateral (FIG. 7A) and oblique (FIG. 7B) views.

Figure 8A:
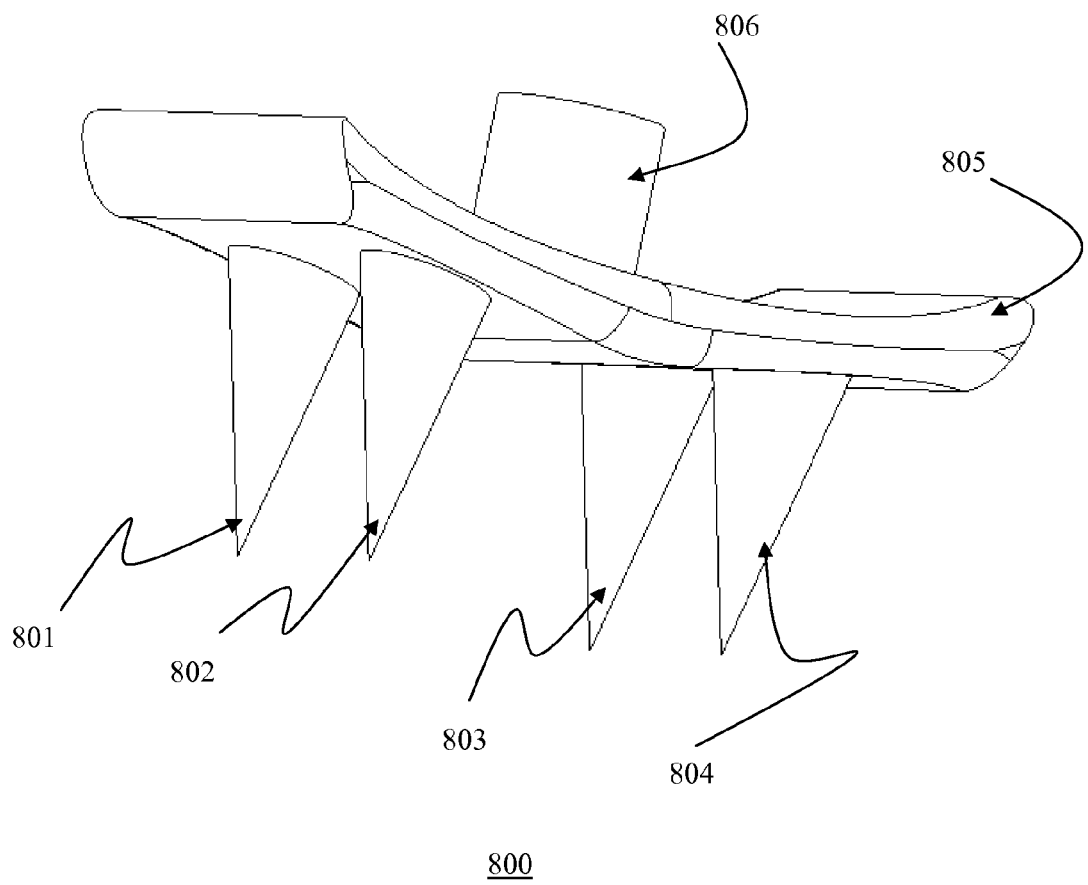
Figure 8B:
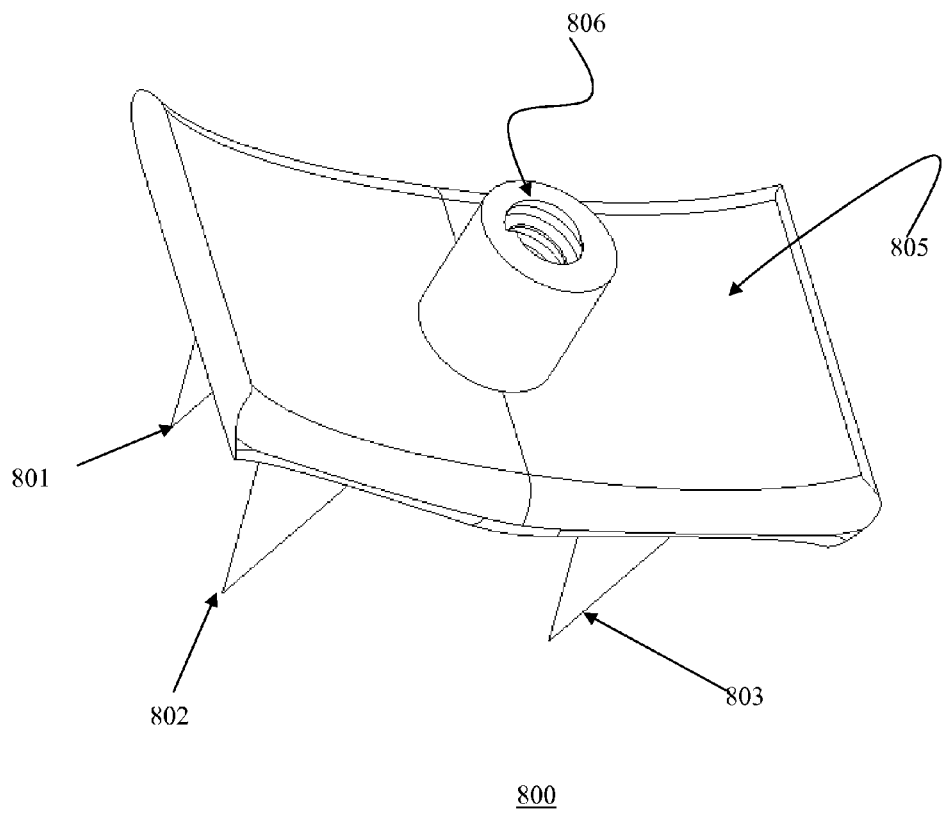
Figure 8C:
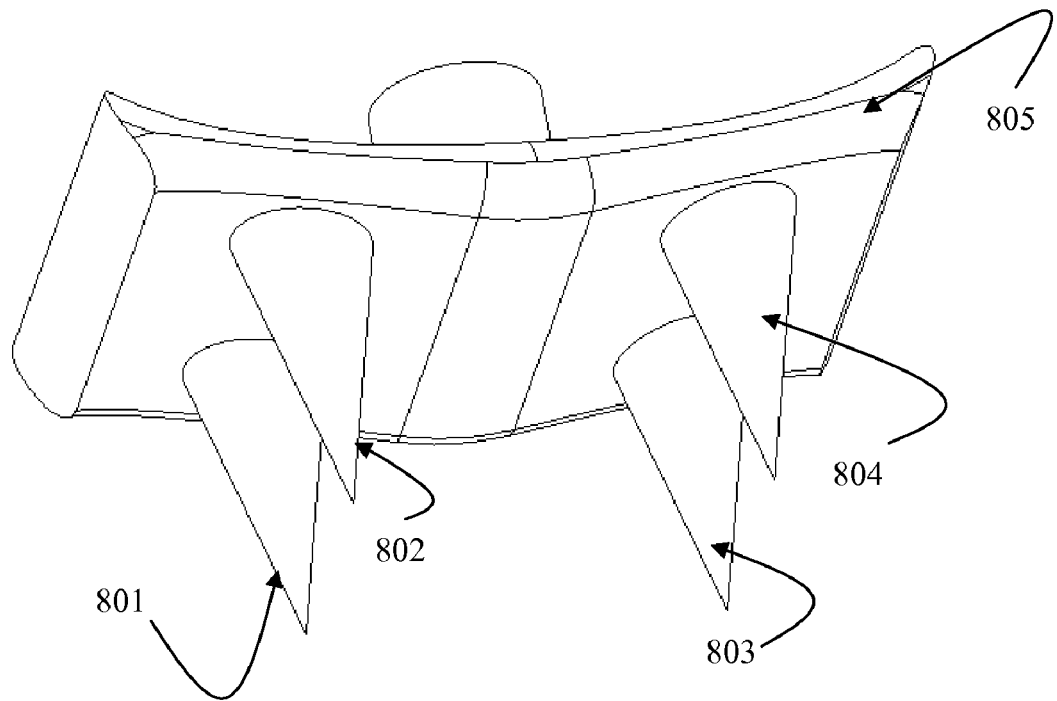

FIG. 8A-C illustrate the cervical facet staple (Embodiment II) in oblique (FIG. 8A), superior perspective (FIG. 8B) and inferior-oblique (FIG. 8C) views.

Figure 9A:
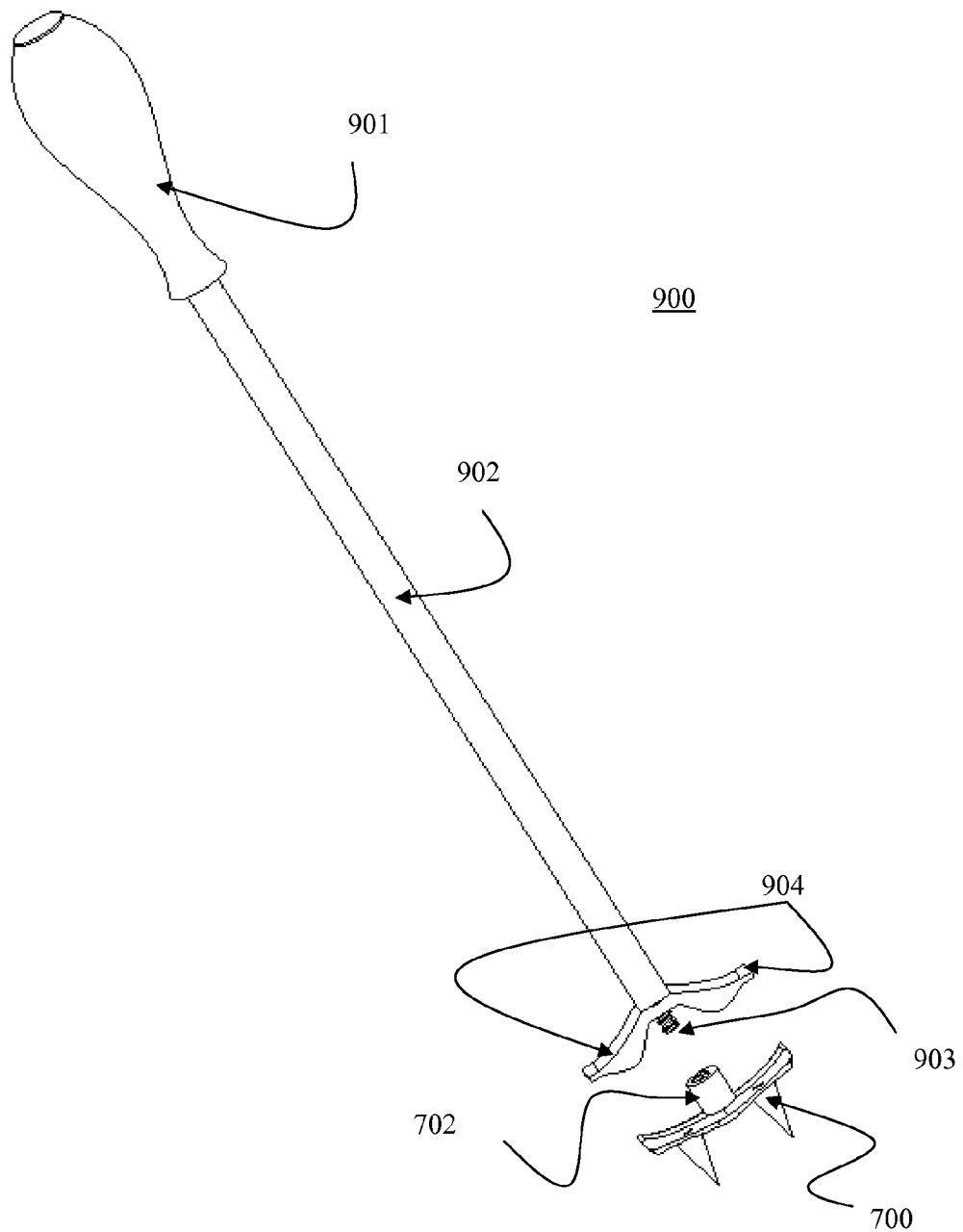

FIG. 9A illustrates the two-pronged cervical facet staple inserter/impactor (Embodiment I).

Figure 9B:
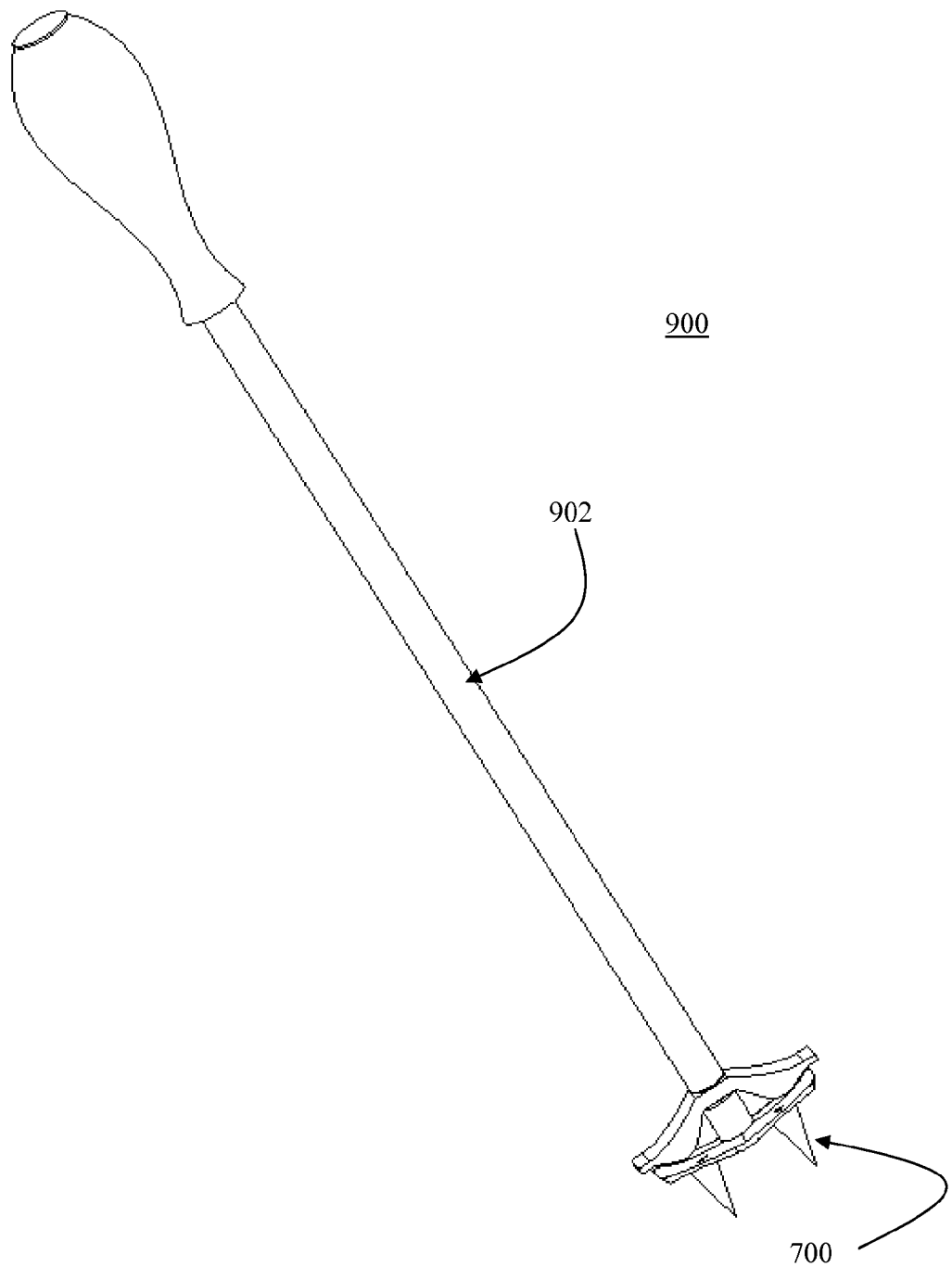

FIG. 9B illustrates the two-pronged cervical facet staple inserter/impactor inserted into the staple (Embodiment I).

Figure 10A:
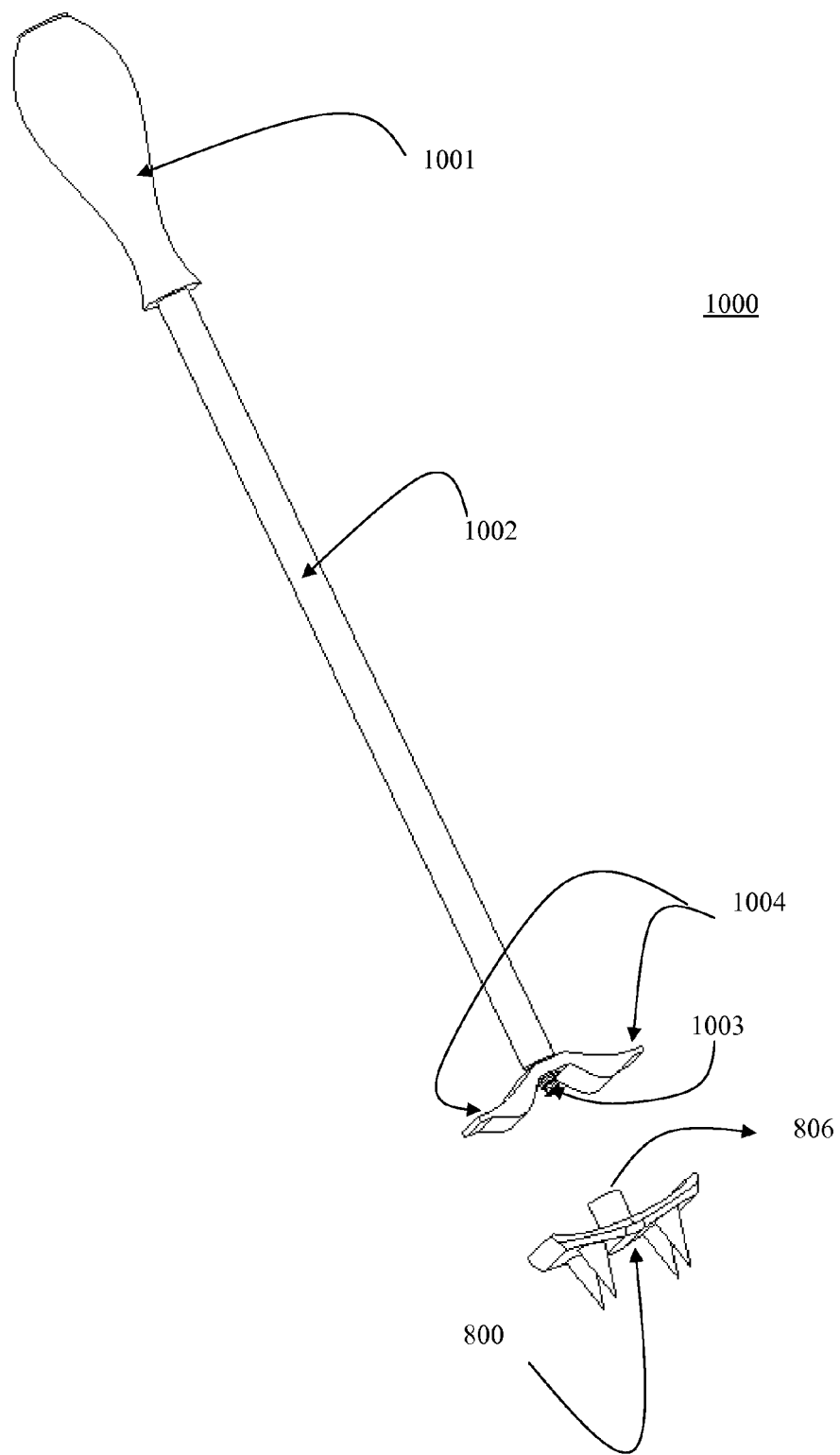

FIG. 10A illustrates the four pronged cervical facet staple impactor (Embodiment II).

Figure 10B:
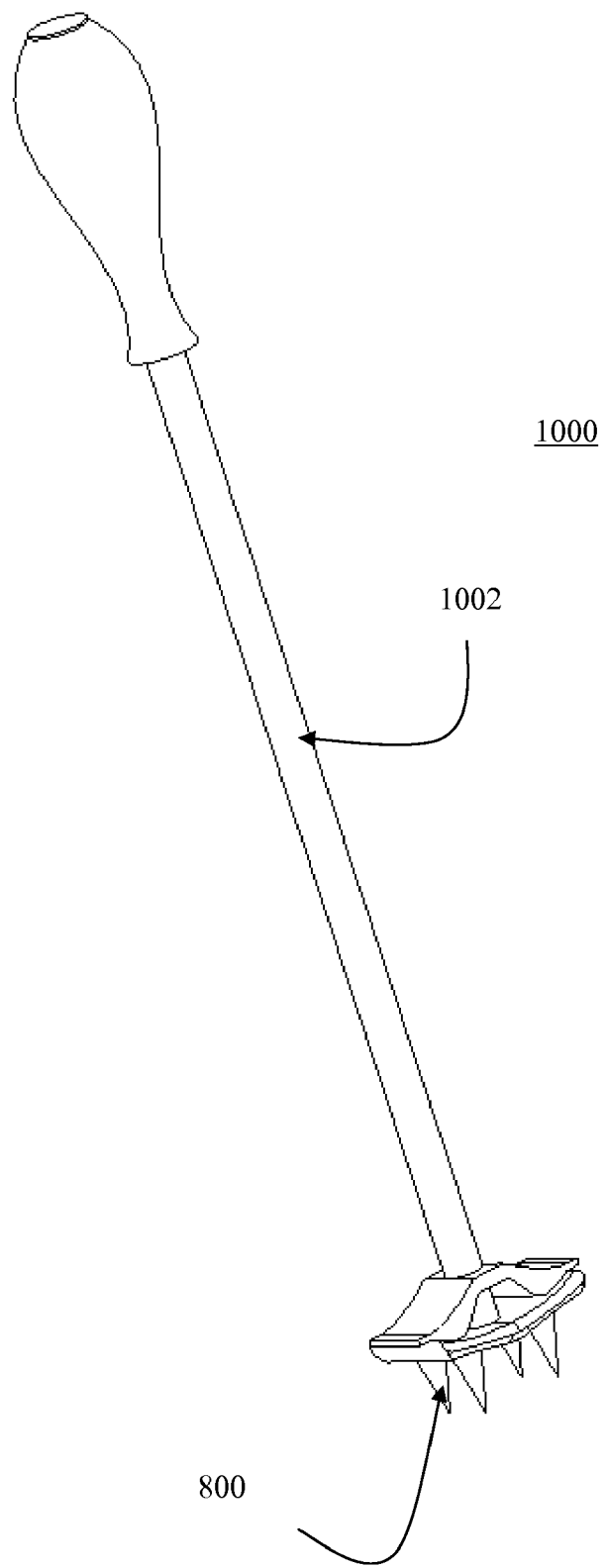

FIG. 10B illustrates the four pronged cervical facet staple impactor inserted into the cervical facet staple (Embodiment II).

Figure 10C:
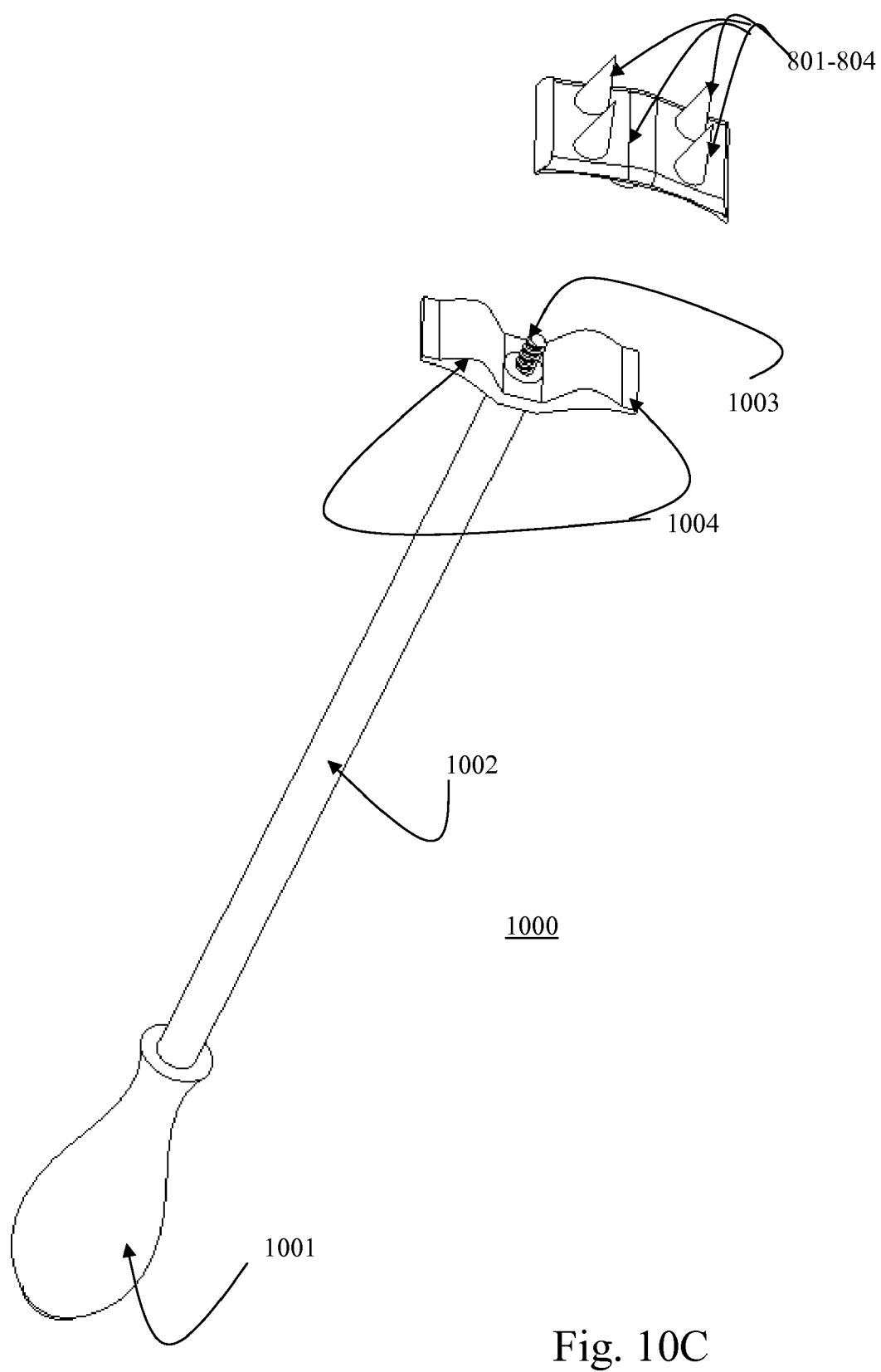

FIG. 10C illustrates an inferior-oblique perspective view of the four-pronged cervical facet staple impactor (Embodiment II).

Figure 11A:
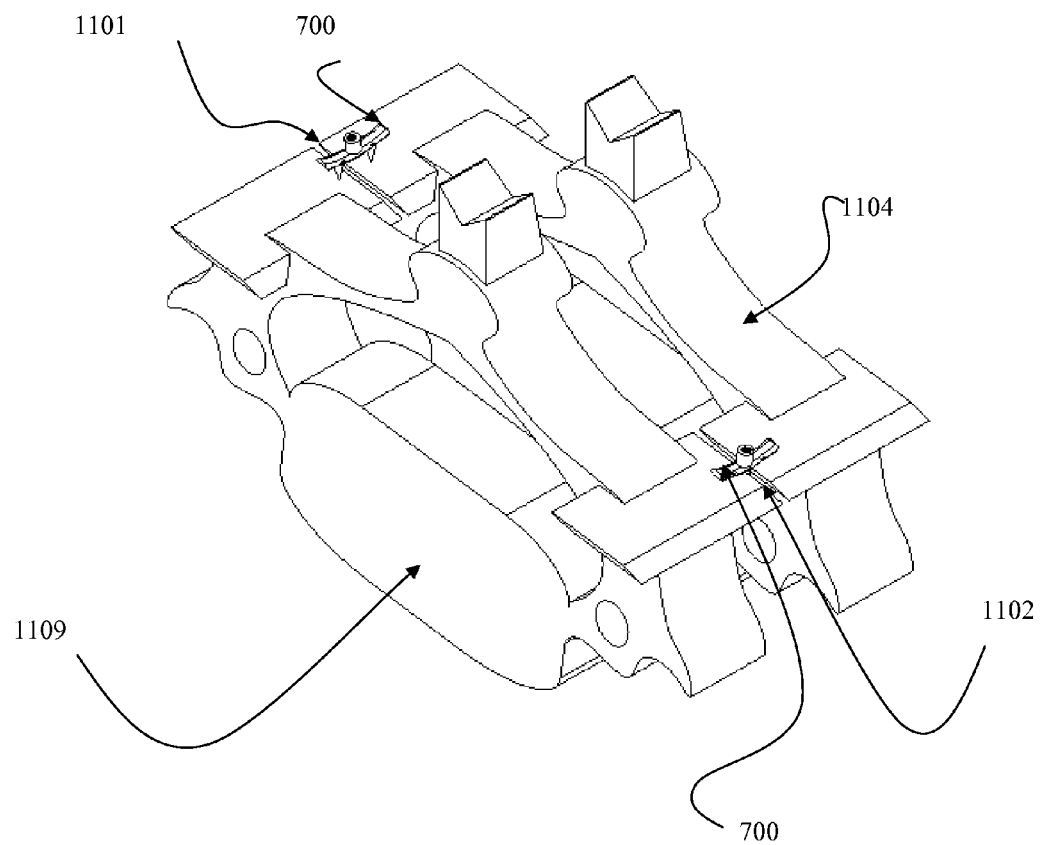

FIG. 11A illustrates placement of two-pronged cervical facet staples in a three-dimensional cervical spine.

Figure 11B:
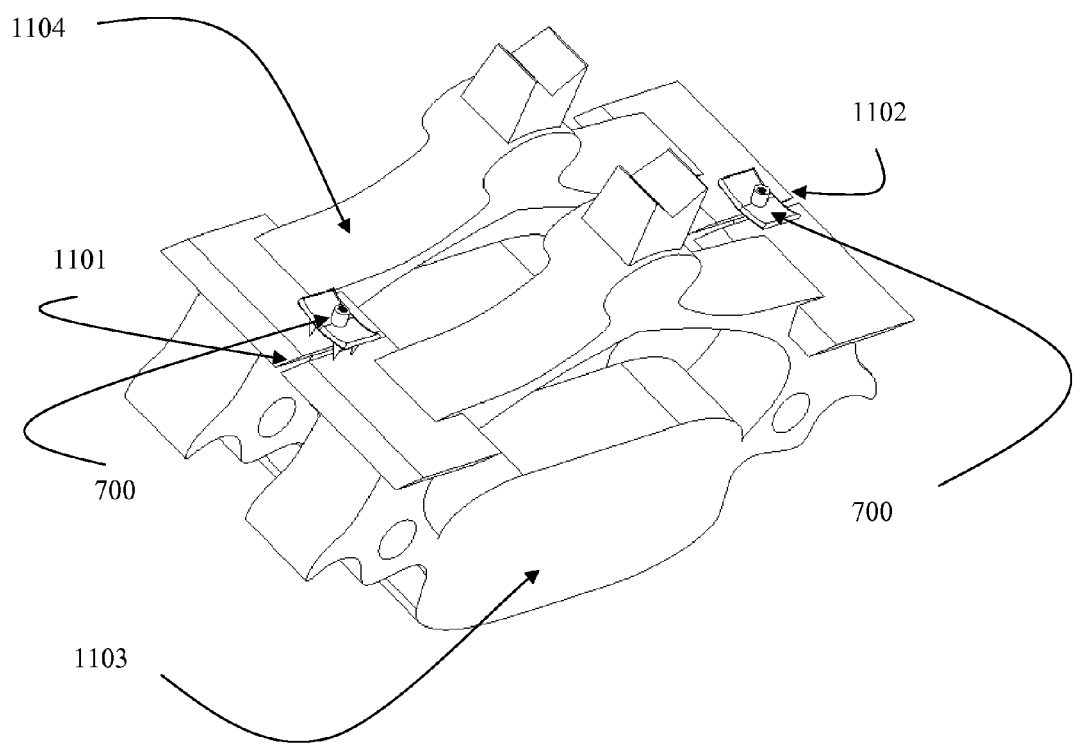

FIG. 11B illustrates placement of four-pronged cervical facet staples in a three-dimensional cervical spine.

Figure 11C:
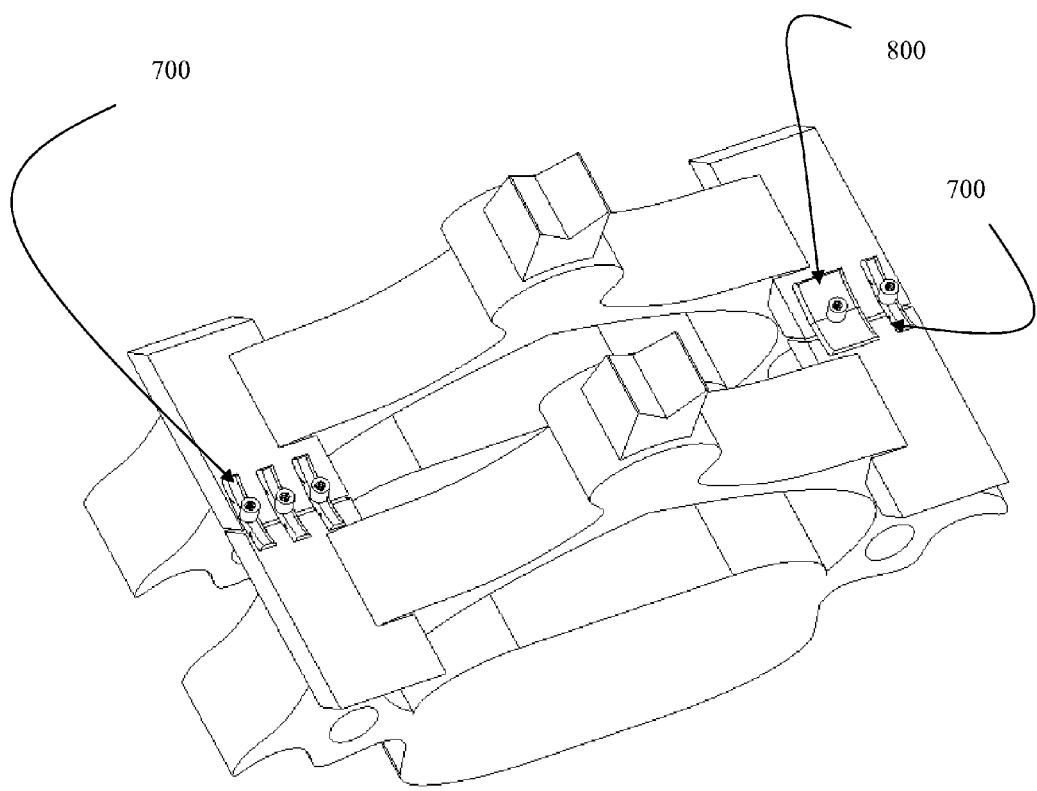

FIG. 11C illustrates modular placement of two and four pronged cervical facet staples in a three-dimensional cervical spine to achieve differing calibrated degrees of flexibility.

Figure 12A:
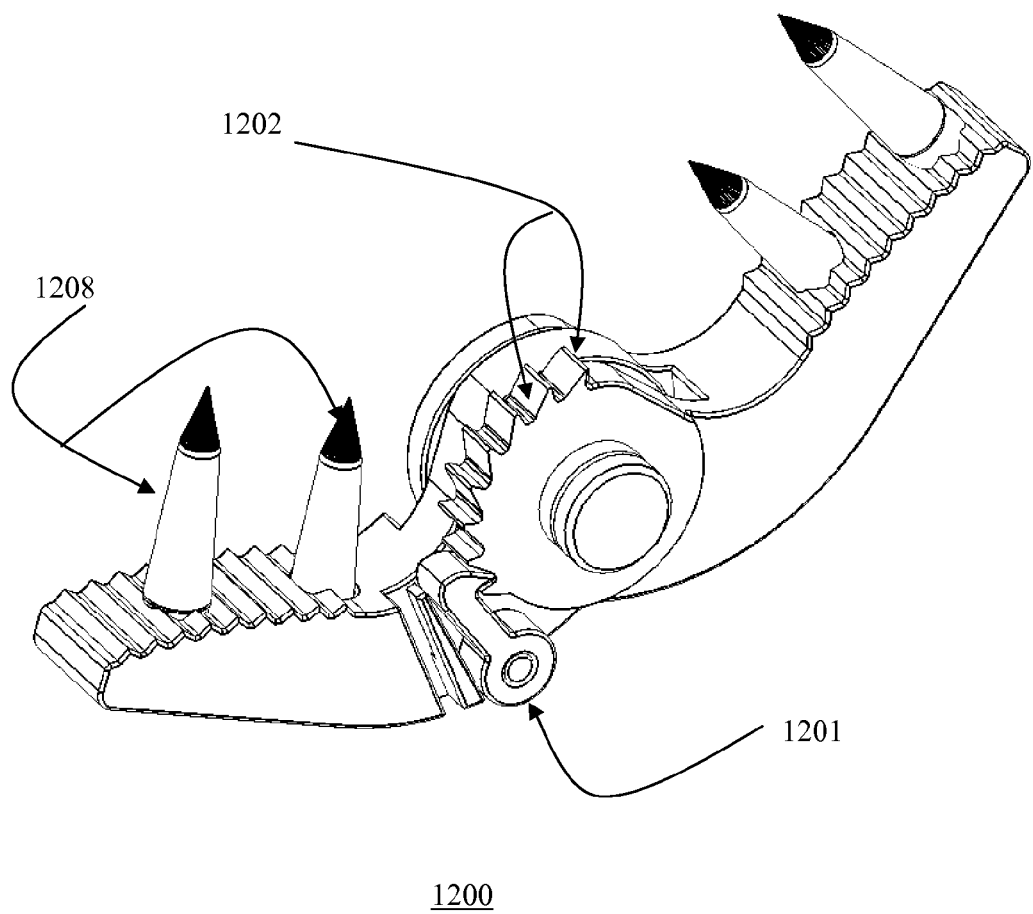
Figure 12B:
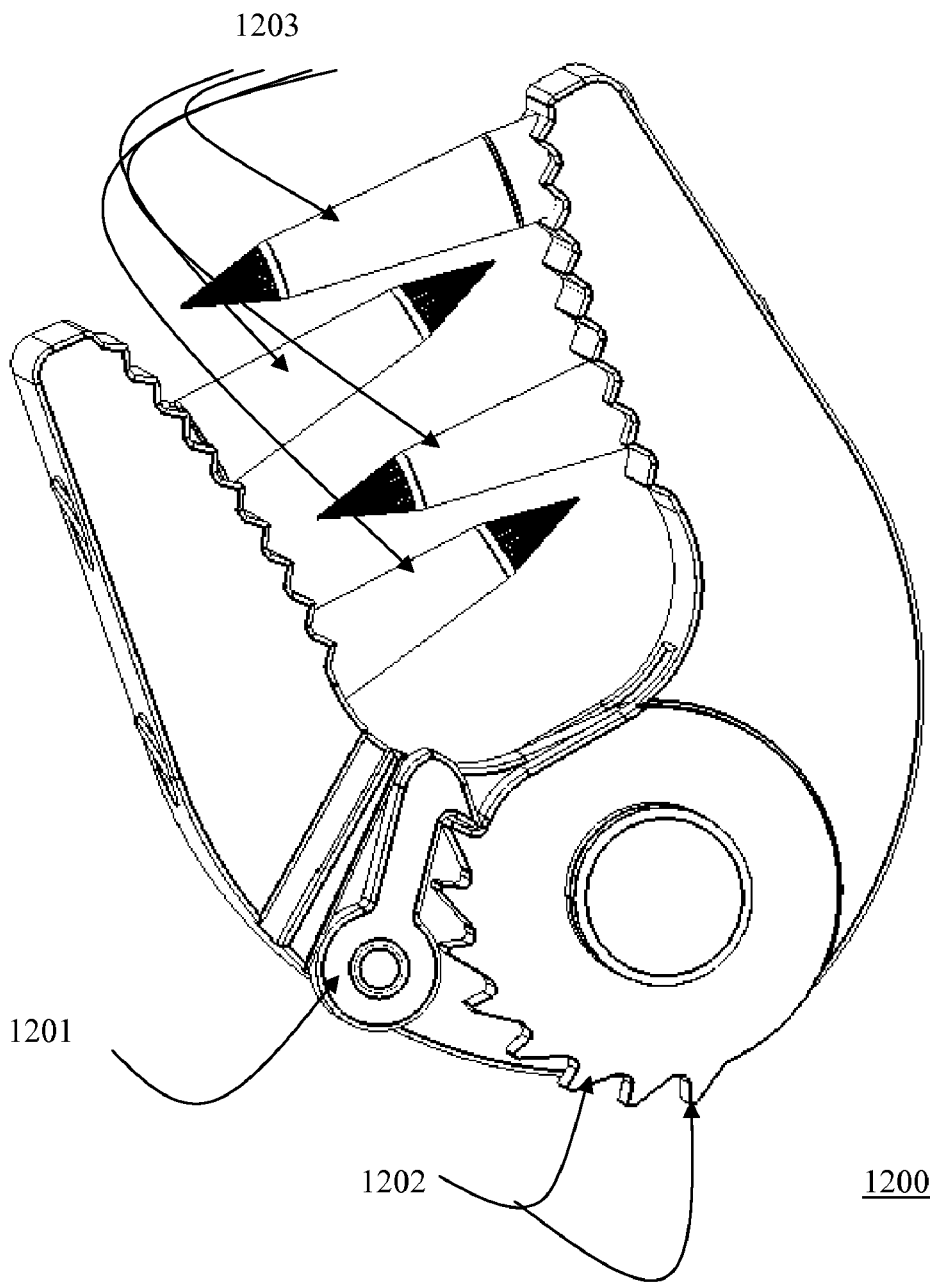

FIGS. 12A-B illustrate the Lumbar facet joint staple with a calibrated ratcheting mechanism in opened (FIG. A) and closed (FIG. B) positions.

DETAILED DESCRIPTION OF THE INVENTION

1. The Medical Device

Referring to FIGS. 1-6, the above described problem can be solved in the thoracic and lumbar spine by insertion into the denuded intervertebral disc space multiple embodiments of screw box constructs with BDFT screws.

Figure 1A:
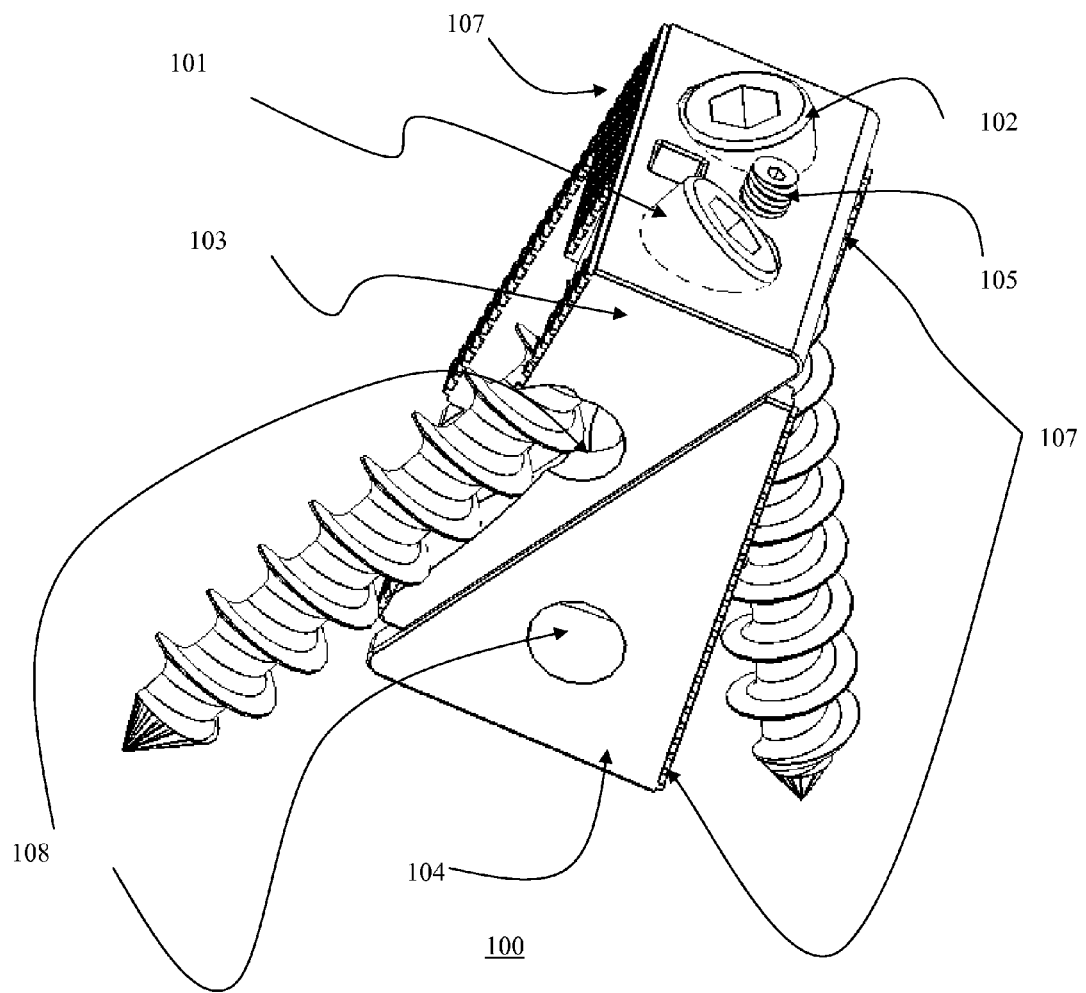
FIGS. 1A-D illustrate the Lumbar expandable intervertebral screw box with one lateral oriented BDFT screw and one medially oriented BDFT screw (Embodiment IA) in sagittal-oblique (FIG. 1A), superior perspective (FIG. 1B), inferior perspective (FIG. 1C) and exploded (FIG. 1D) views.
Figure 1B:
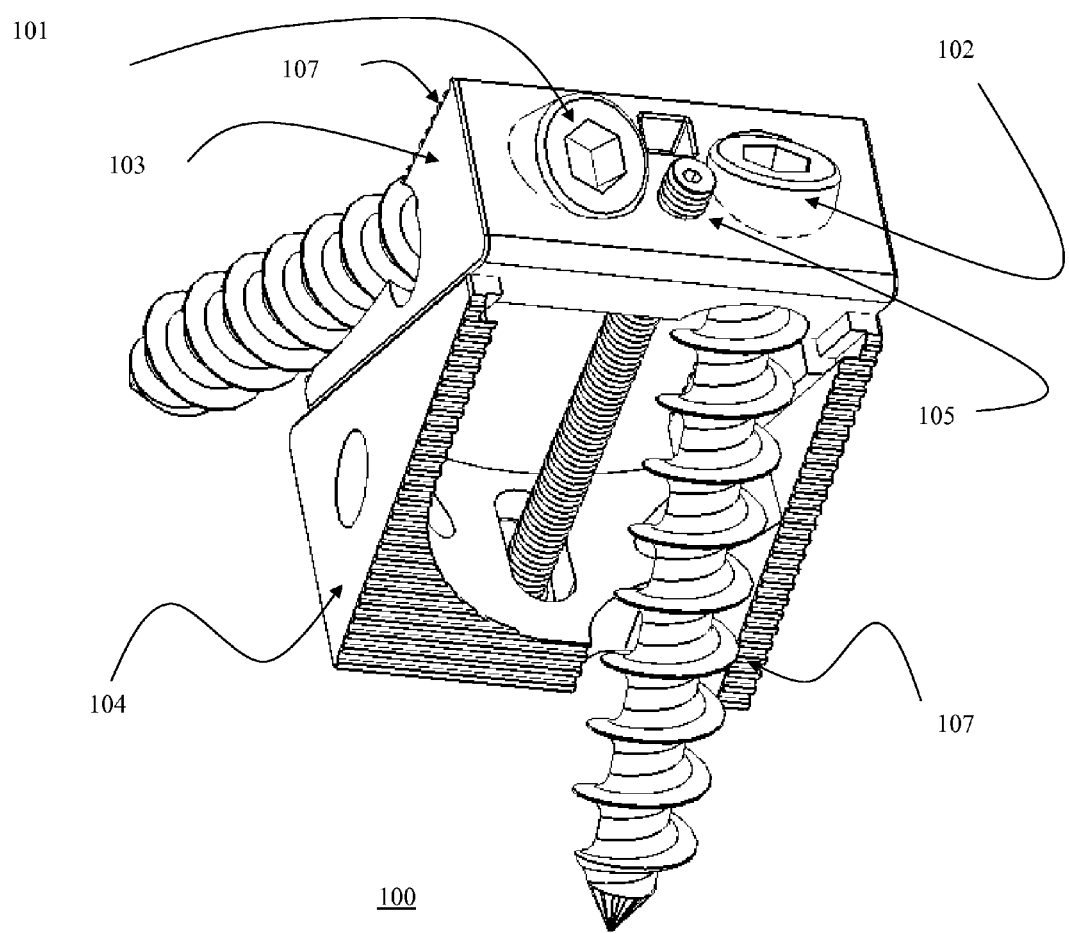
Figure 1C:
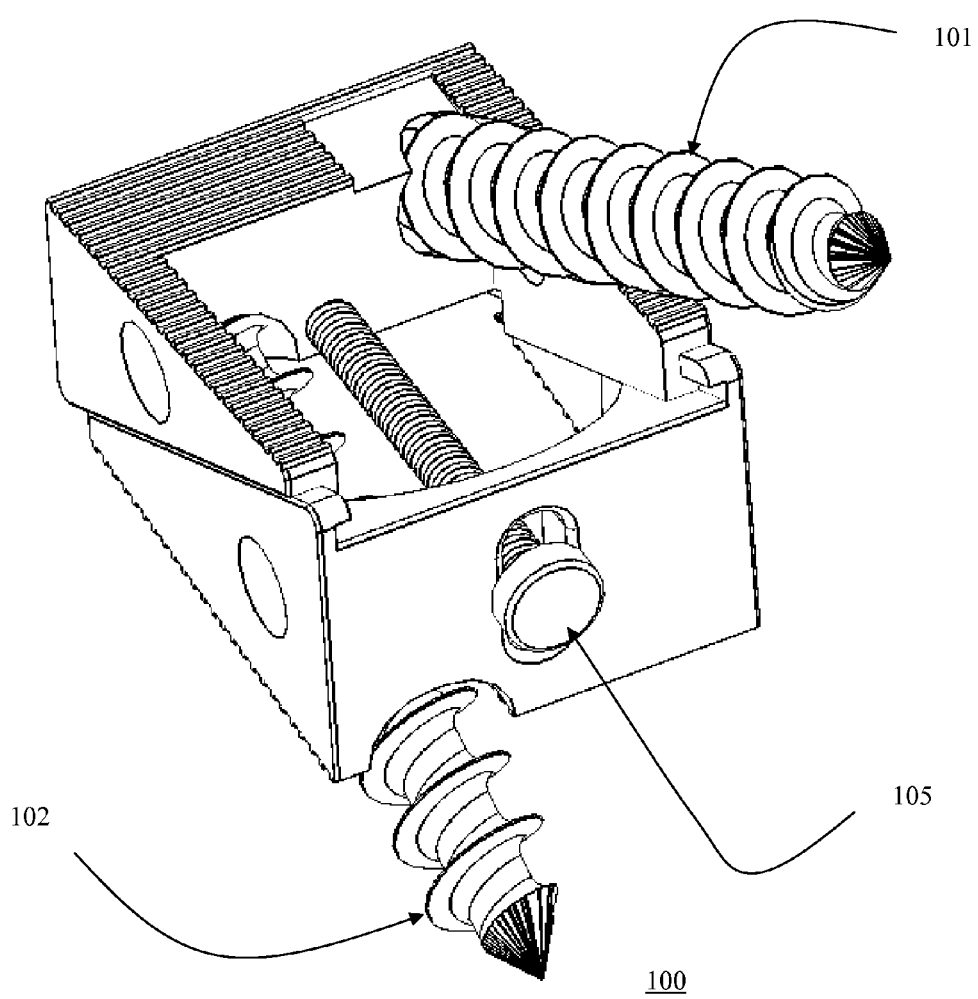
Figure 1D:
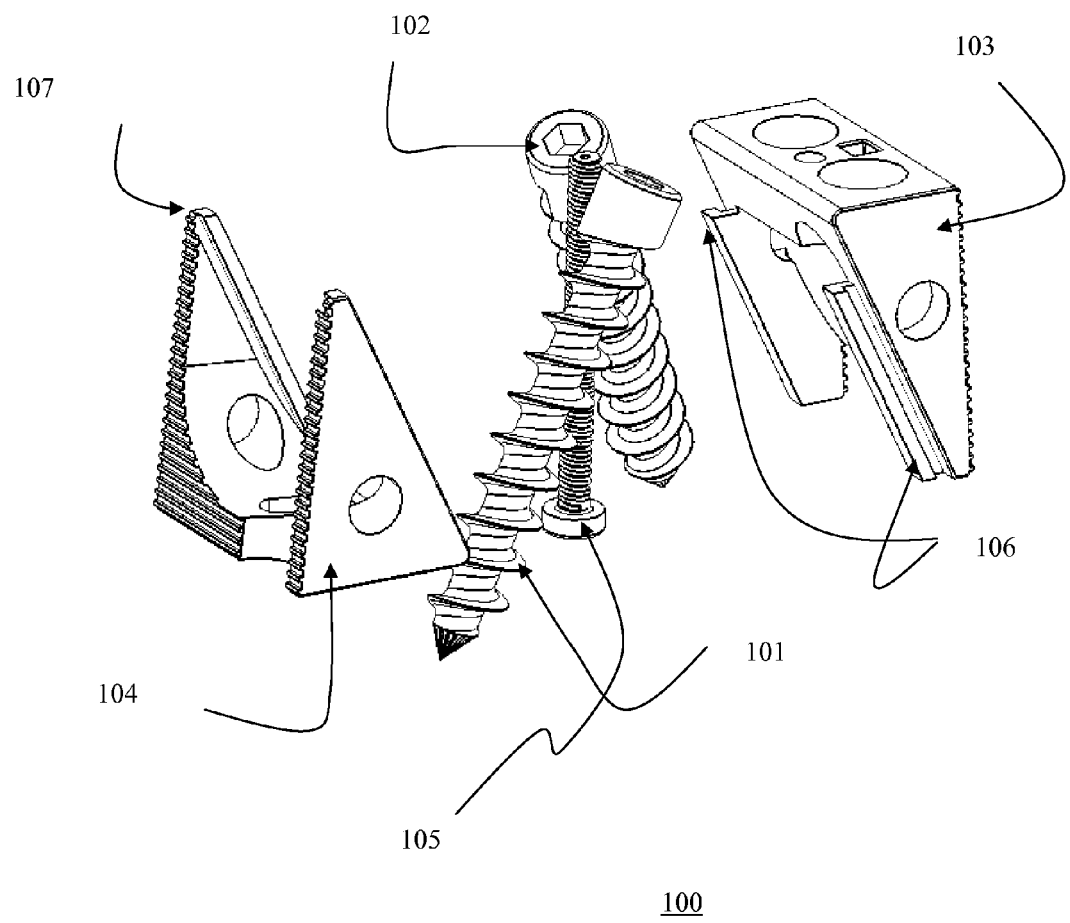
Figure 1E:
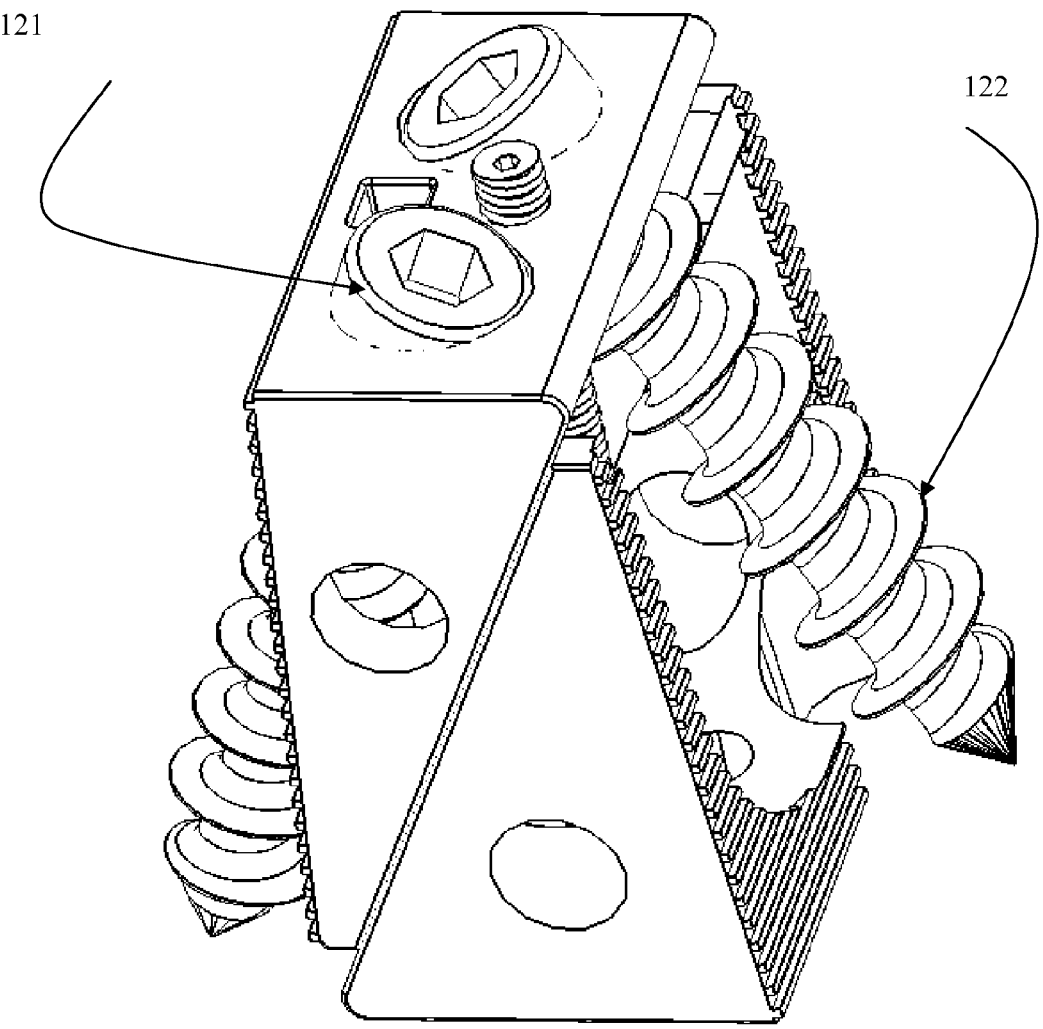
FIG. 1E illustrates the lumbar intervertebral expandable screw box with two lateral oriented BDFT screws (Embodiment IB; sagittal-oblique view).

FIGS. 1A-D illustrate three-dimensional views of the Lumbar intervertebral expandable screw box 100 with two BDFT screws 101, 102; one lateral and one medially oriented (Embodiment IA). FIG. 1E illustrates a sagittal-oblique view of the lumbar intervertebral expandable screw box 120 with two lateral oriented BDFT screws 121, 122 (Embodiment IB).

The expandable box 100 consists of top and bottom triangular sliding bases 103, 104 (FIG. 1-D). The superior and inferior segments of the height/depth adjusting screw 105 are integrated and connected to the two separate top and bottom triangular bases 103, 104, respectively. By turning this adjusting screw 105 back and forth i.e. clock-wise, and counter clockwise, the sliding rails 106 of the top triangular base 103 (FIG. 1D) slide up and down the rail inserts 107 on the bottom triangular base 104 (FIG. 1D). This action will simultaneously alter the intervertebral height and depth of the screw box 100 allowing individualized custom fitting of the screw box 100 conforming to the dimensions of the disc space.

Transvertebral screw 101 penetrates the top base 103, and transvertebral screw 102 traverses the bottom base 104 of the screw box 100. The two screws 101, 102 traverse the screw box 100 in opposing directions, bi-directionally (whether they are lateral or medially oriented). The external edges of the triangular bases 103, 104 in contact with vertebral body surfaces include ridges 107. This facilitates the screw box's 100 incorporation into and fusion with the superior and inferior vertebral bodies (FIGS. 1A-E). Both top and bottom screw box bases 103, 104 are perforated with holes 108 to allow bone placement for fusion. The entire construct, furthermore, is hollow to allow bone filling. Hence this device functions as both an intervertebral bone fusion spacer and bi-directional transvertebral screw fusion device.

Figure 2A:
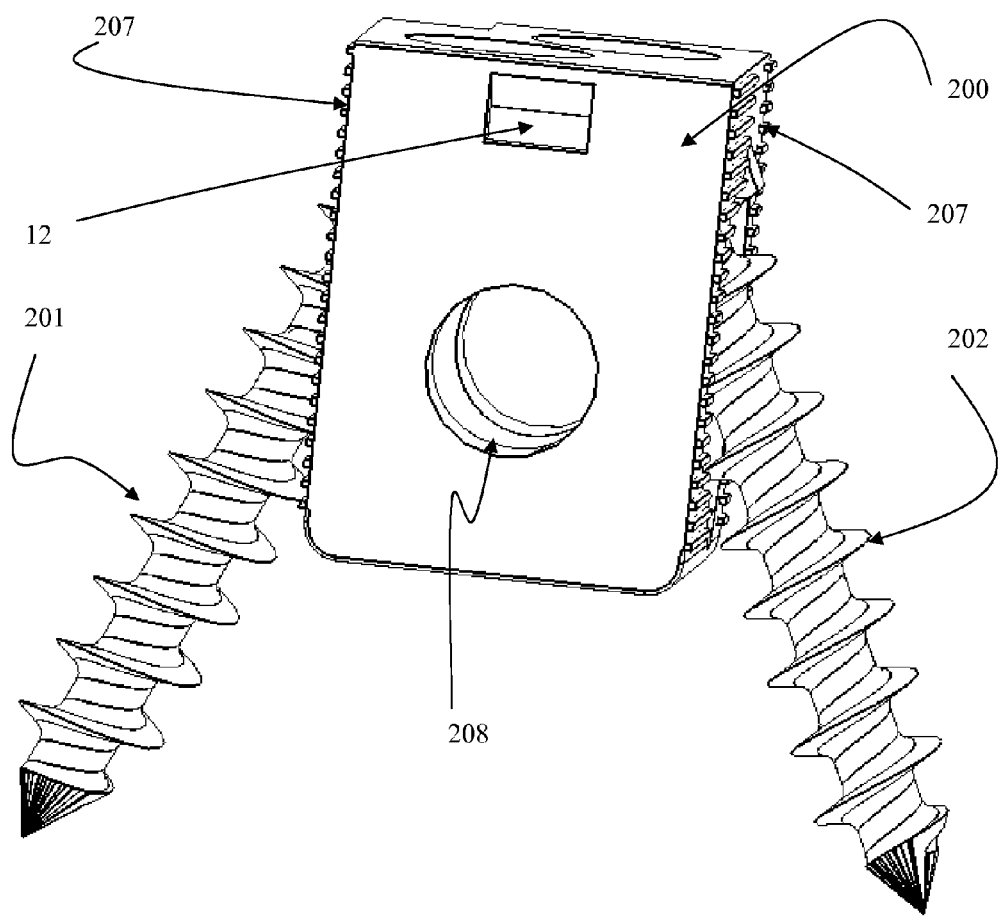
FIGS. 2A-2E illustrate the Lumbar intervertebral non-expandable screw box with two BDFT screws (Embodiment II) in lateral (FIG. 2A), oblique (FIG. 2B), and superior perspective (FIG. 2C) views, and again in superior perspective (FIG. 2D) and superior perspective (FIG. 2E) with gridlines.
Figure 2B:
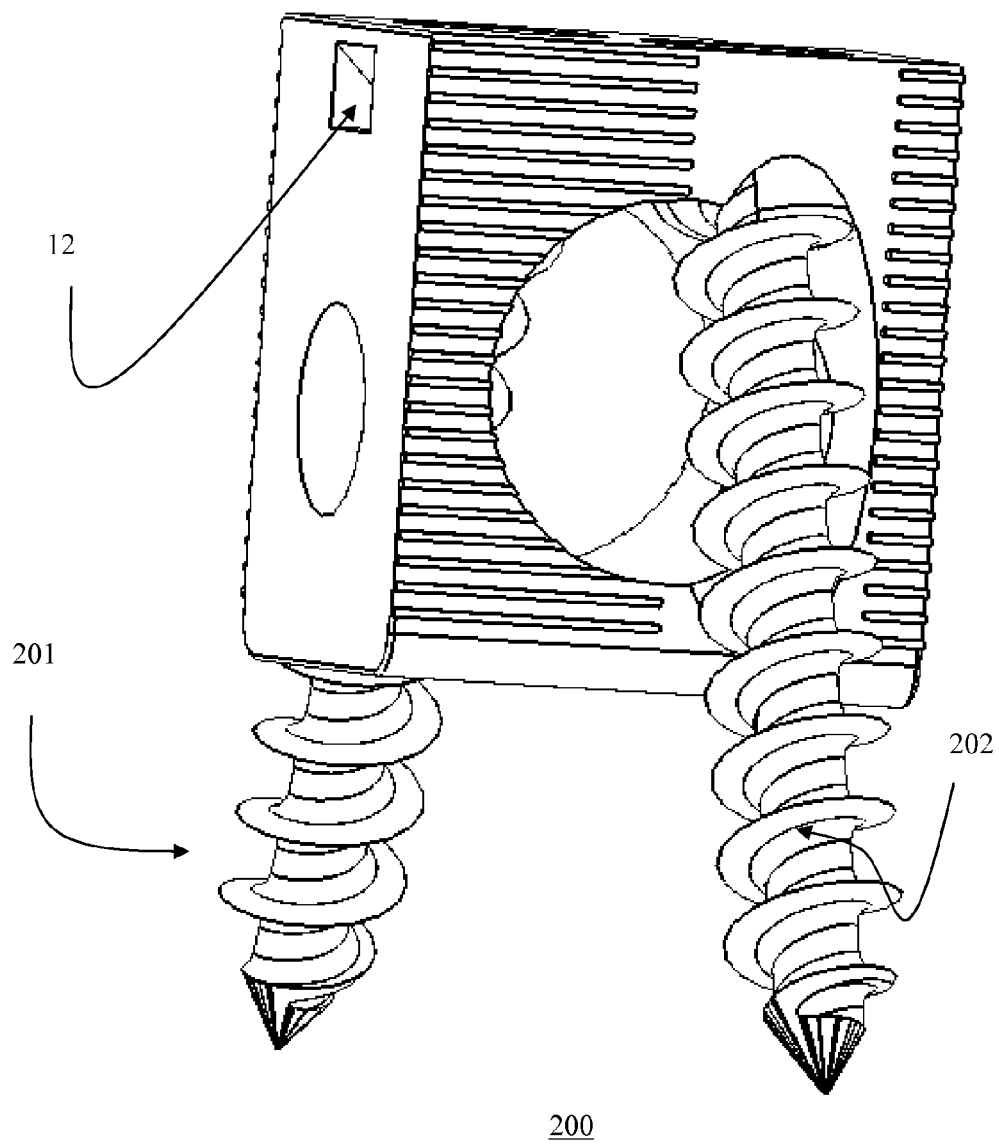
Figure 2C:
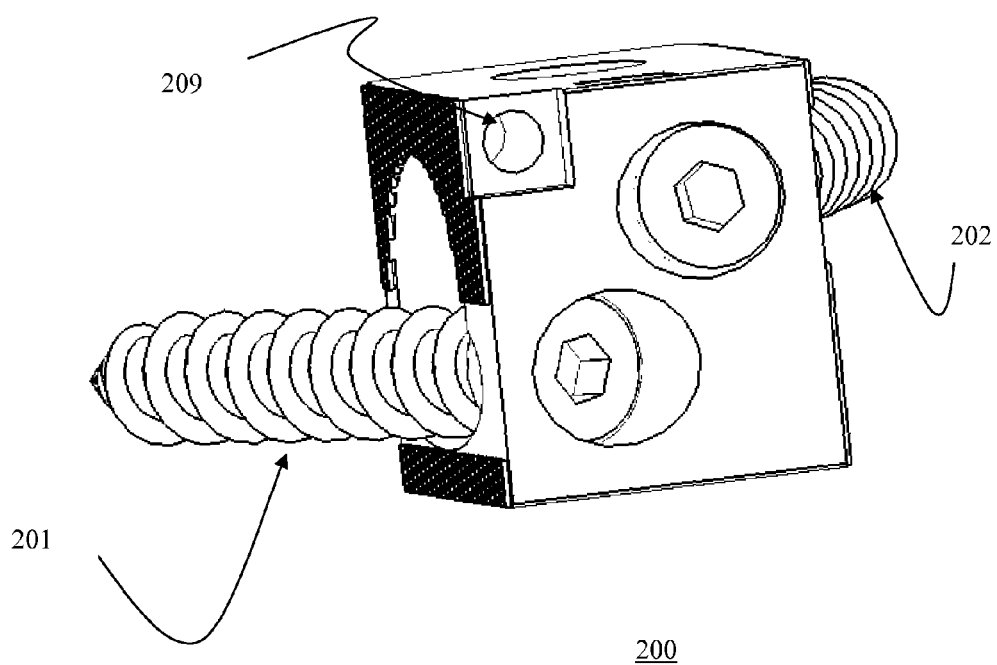
Figure 2D:
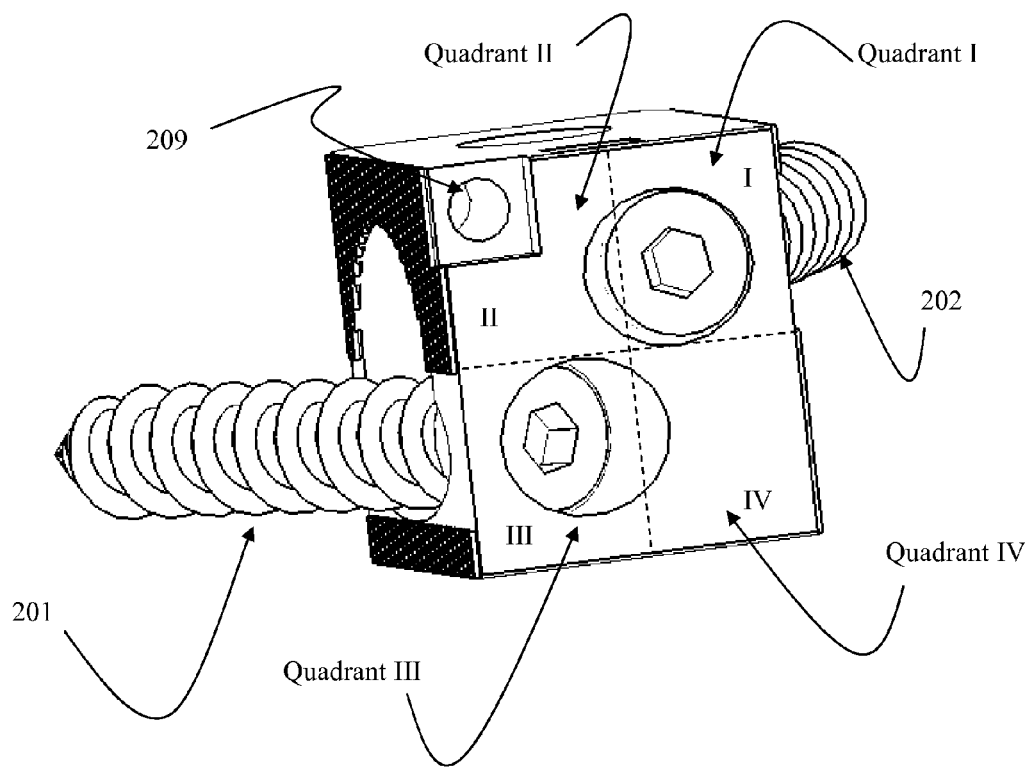
Figure 2E:
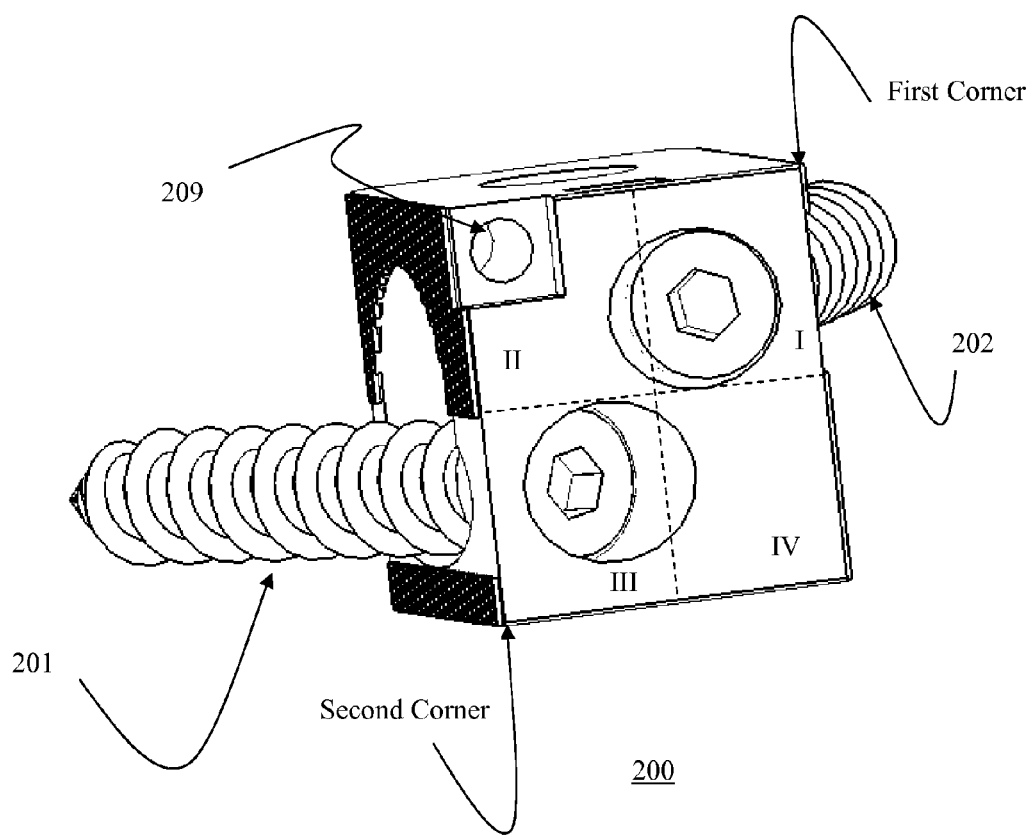

FIGS. 2A-2E illustrate three-dimensional views of the Lumbar intervertebral non-expandable screw box 200 with two BDFT screws 201, 202 (Embodiment II). Screws 201 and 202 perforate and orient in opposing, superior and inferior directions. There are holes 208 and hollow spaces allowing packaging with bone. There are also holes which allow the traversal of screws. The superior and inferior edges include ridges 207 to facilitate integration and fusion with superior and inferior vertebral bodies. The expandable screw box 200 may include a screw insert 209 to attach a horizontal mini-plate (not shown). The self-contained internalized drill guides are at a 25 degree angle. The screw boxes can be designed with the internalized drill guides with different angles and/or different positions within the box. As shown in FIGS. 2A and 2B, each longitudinal end of the screw box 200 can include a slot or indentation 12 formed adjacent to an edge of an upper surface of the screw box 200 for engaging a protuberant extension of a tool (as shown in FIGS. 5A-5J).

Figure 3:
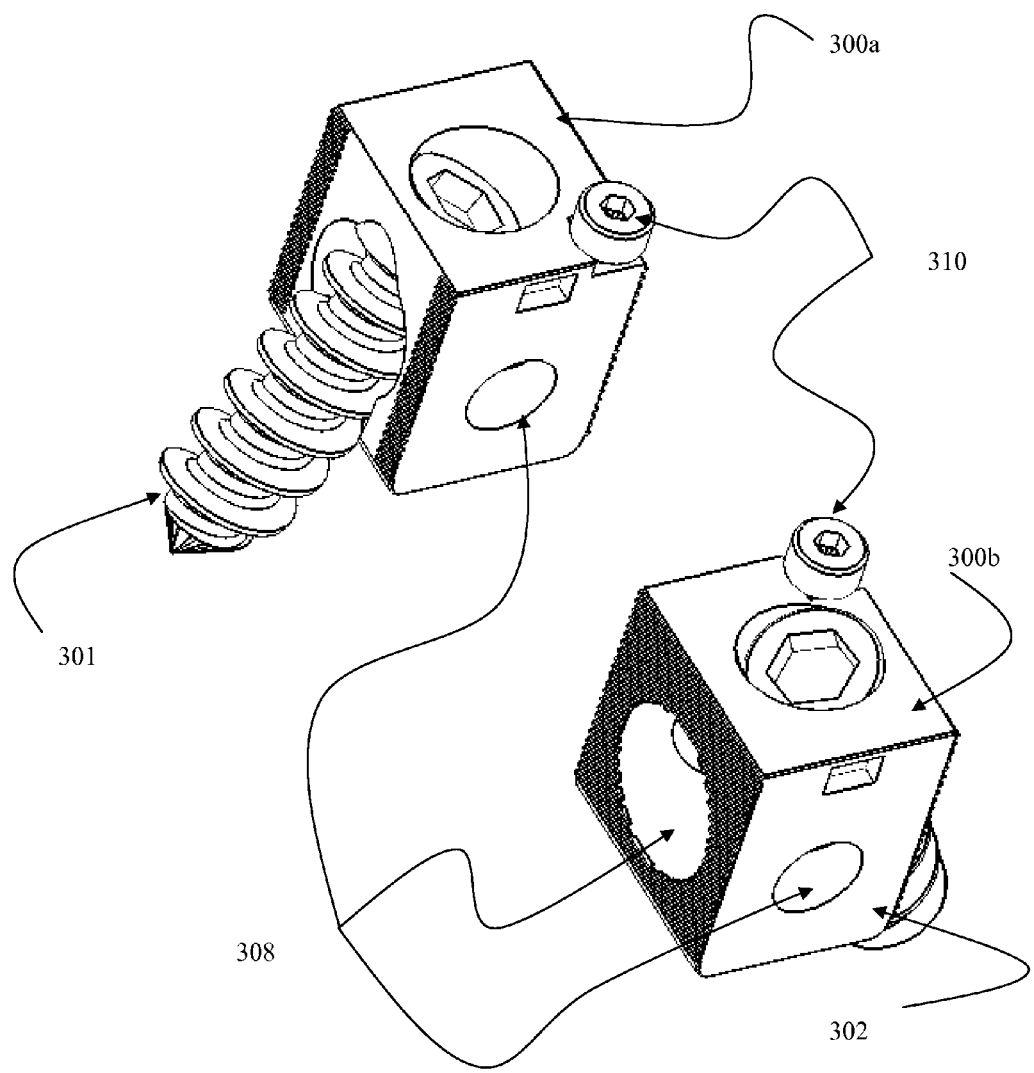
FIG. 3 illustrates a superior oblique perspective view of left and right lumbar intervertebral non-expandable screw boxes with one BDFT screw (Embodiment III).

FIG. 3 illustrates a three-dimensional view of left and right lumbar intervertebral non-expandable screw boxes 300a, 300b with one BDFT screw 301 or 302 (Embodiment III). It is roughly half the width of Embodiments I and II. Screw 301 is inserted into screw box 300a (left) and screw 302 is inserted into screw box 300b (right). There are holes 308 and hollow spaces allowing packing of bone to achieve biological fusion. The combined effect of one superior oriented and one inferior oriented screw fuses the superior and inferior vertebral bodies with small constructs. This also enables placement of larger dimension screws compared to embodiments I and II.

Figure 4A:
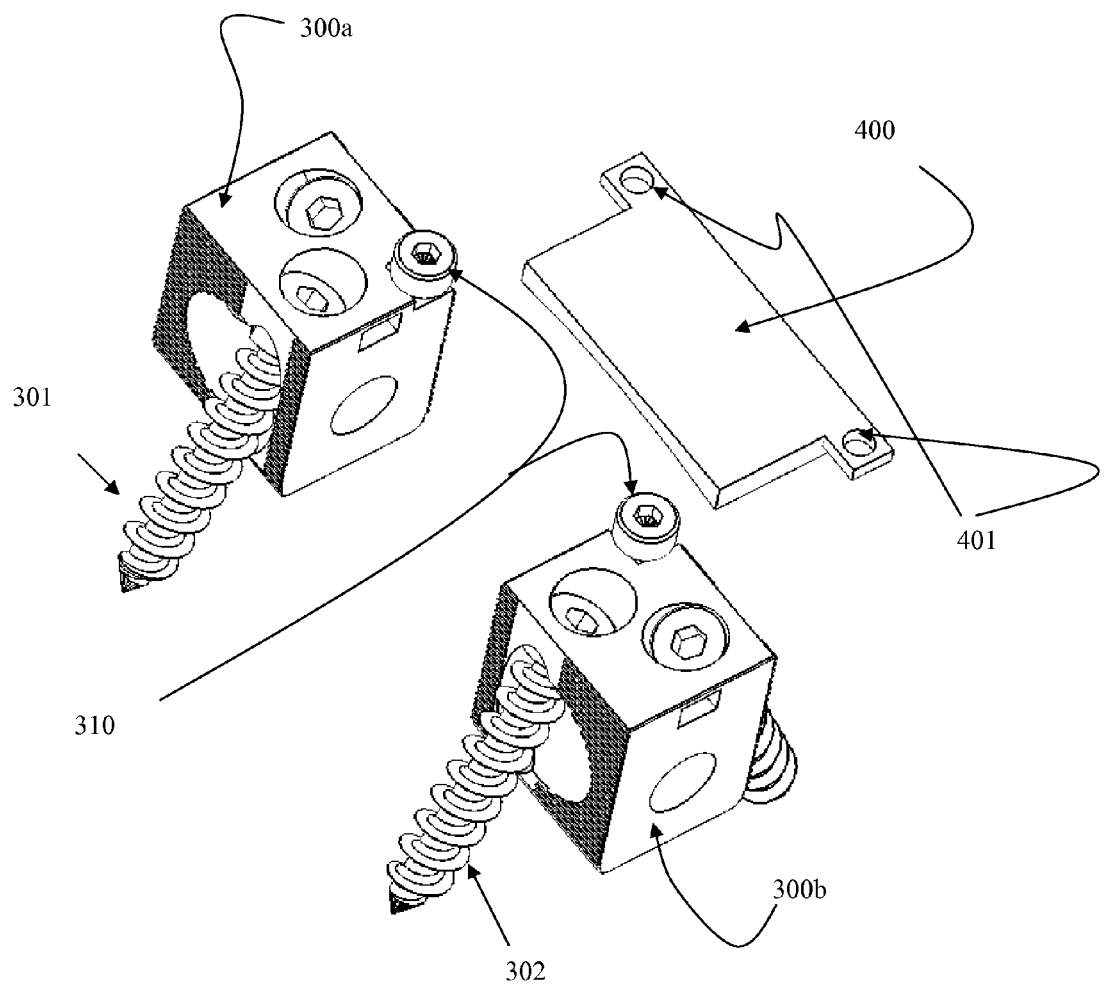
FIGS. 4A-B illustrate the horizontal intervertebral zero-profile mini-plate prior to insertion (FIG. 4A), and after insertion (FIG. 4B) into two non-expandable lumbar intervertebral screw boxes with two BDFT screws.
Figure 4B:
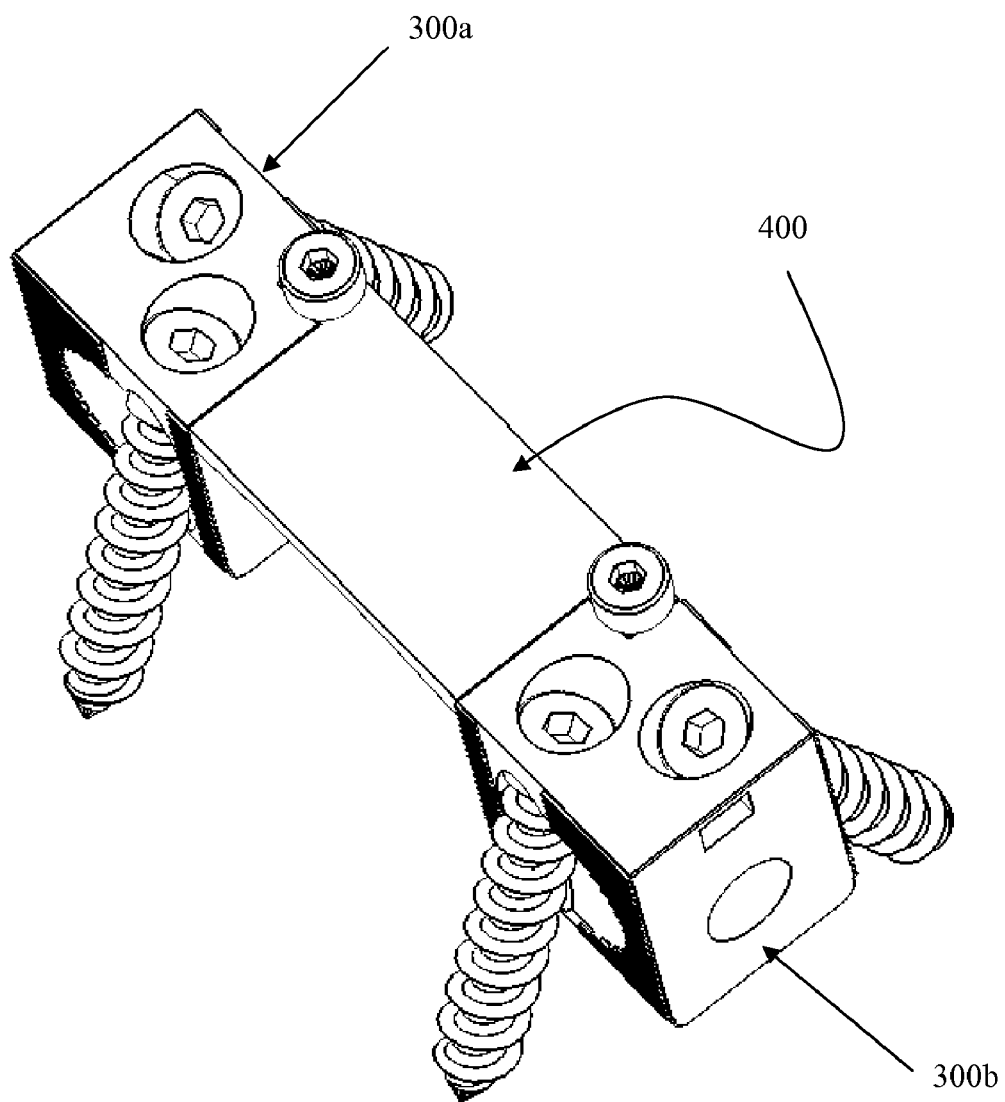

FIGS. 4A and B illustrate three-dimensional views of the horizontal intervertebral zero profile mini-plate 400 with two non-expandable lumbar intervertebral screw boxes 300a, 300b housing two BDFT screws 301, 302. FIG. 4A illustrates the perforations 401 within the plate 400 through which small plate securing screws 310 will be inserted to connect it to the built-in screw holes of the screw box 300a, 300b (FIG. 4B). The horizontal mini-plate 400 together with the top surfaces of left and right screw boxes 300a, 300b provide a physical barrier between the underlying bone placed beneath it (not illustrated), and the thecal sac and nerve roots above it (not illustrated).

Figure 4C:
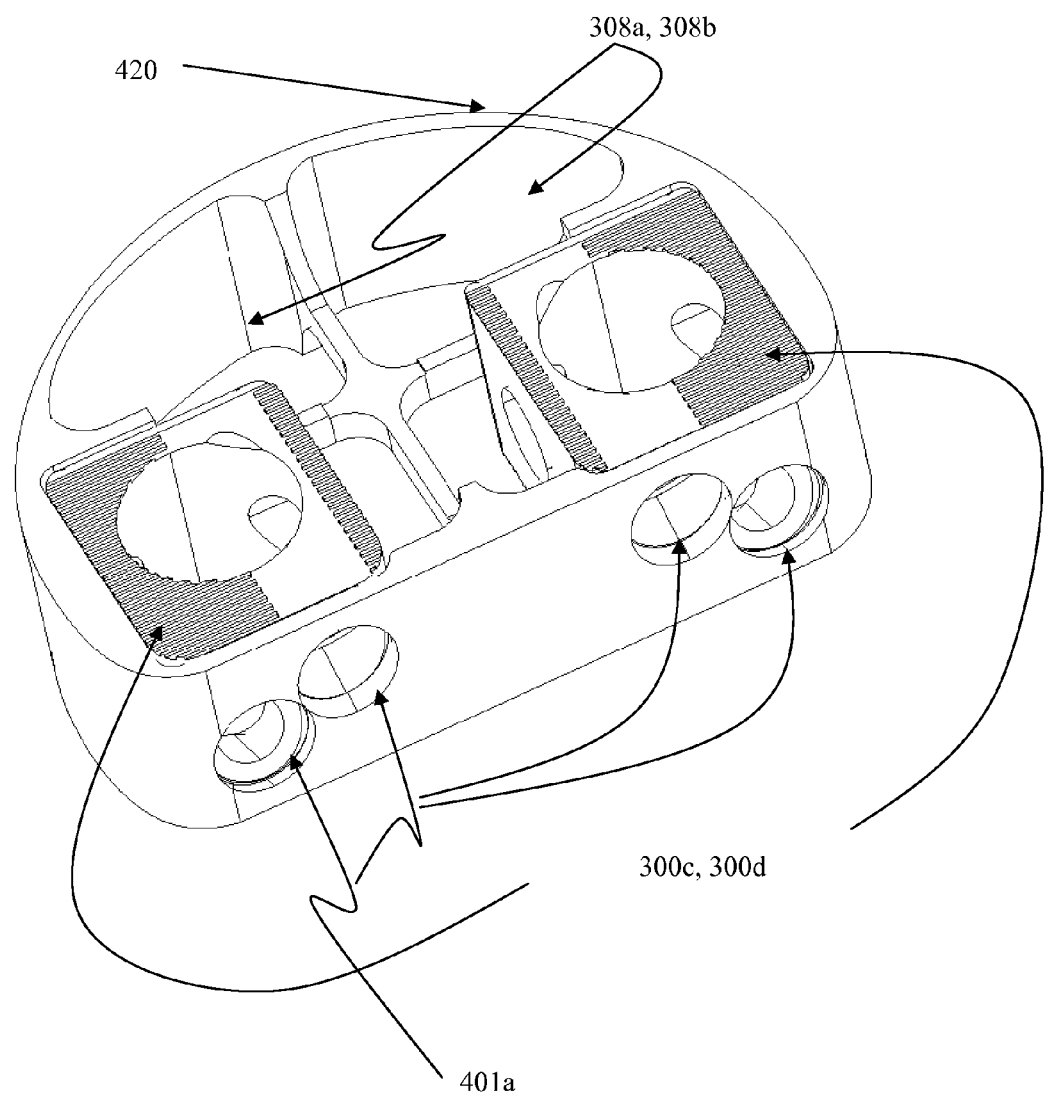
FIG. 4C illustrates two non-expandable lumbar intervertebral screw boxes with two screws within a large circumferential cage for anterior placement into the lumbar spine

FIG. 4C illustrates two screw boxes 300c, 300d within a circumferential cage 420 (2 in 1) construct which is designed for anterior placement into the lumbar spine. There are slots 308a, 308b for bone graft placement, both outside and inside the boxes. The circumferential cage 420 has perforations 401a for the placement of transvertebral screws (not shown).

FIGS. 5A-C illustrate three-dimensional views of the external drill/screw guide-box expander 500 which assists in screw trajectory and box expansion (embodiments IA-B). For embodiments II and III, the same instrument is utilized; however, an expanding Allen key component is not used.

The key components of this device include an Allen key 501, a spring 502, a handle 503, a griper 504 and a screw guide 505. The Allen key 501 when inserted in the insertion 514 and turned, turns the screw adjuster (FIG. 5C) which in turn regulates top and bottom triangular screw box base sliding, and hence box 200 width and depth. The griper 504 has griper prongs 506 which insert into grooves of the screw guide 505. The griper prongs 506 include medially oriented male protuberant extensions 506a that engage the slot or indentation 12 of and the screw box 200 (FIGS. 5A-D) thus perfectly aligning them.

FIGS. 5D and 5J illustrate a superior oblique view of the screw guide 505 demonstrating insertions 509 for griper prong 506, built-in trajectory guides 511, 512 for insertions of screws 101 and 102, and the Allen key 501.

FIGS. 5E-G illustrate three-dimensional views of the sequential steps necessary for the external guide assembly. FIG. 5E illustrates the insertion of the Allen key 501 into the handle 503. FIG. 5F illustrates the insertion of the handle 503 through the spring 502 and griper 504. FIG. 5G illustrates insertion of the griper 504 into the screw guide 505.

FIGS. 5H-I illustrate three-dimensional views of a positioning tool 500a for impaction and placement of two transvertebral screws 201, 202 in the non-expandable screw box 200. The driver assembly 550 consists of a screw driver 551, a flexible shaft 552 and a square recess bit 553. This facilitates turning the screws 201, 202 into the bone. The flexible shaft 552 facilitates the avoidance of spinous processes which might hinder the screw driving if the shaft 552 were straight. The positioning tool 500a can have a rectangular handle, Embodiment I (FIG. 5H), or a circular handle, Embodiment I (FIG. 5I). This serves to position the screw box within the intervertebral space, and screws 201, 202 within the screw box. Once positioned, the screw box can be impacted by tapping the handle with a mallet (not shown). The positioning tool's 500a griper handle inserts into the screw guide and the box, which maintains alignment.

FIG. 6A illustrates a three-dimensional view of insertion of the construct (Embodiment I) into the lumbar intervertebral disc space.

FIG. 6B illustrates a three dimensional lateral view of insertion of the construct (Embodiment I) into the disc space with short screws. Placement with longer screws would capture more bone.

FIGS. 7A and B illustrate three-dimensional views of the two-pronged cervical facet staple 700 (Embodiment I). There is a staple base 701 which is contoured to align with the curved surface of the cervical facet joints. There is a superior impactor threaded insert 702. An impactor can be screwed into this insert 702 and then impacted with a mallet. The two spikes 703, 704 perforate the inferior and superior facets of the superior and inferior vertebral bodies hence leading to cervical facet joint fusion. The spikes can be designed with ridges and/or fishhooks to facilitate irreversible extraction.

FIGS. 8A-C illustrate three-dimensional views of the four-pronged cervical facet staple 800 (Embodiment II). Likewise it has a staple base 805 contoured specifically for the surface of the facet joint. It also has an impactor insert 806. The insertion of a device with four prongs 801-804 instead of two prongs further limits the degrees of motion of the joint hence making the fusion more rigid.

FIGS. 9 A-B illustrate a three-dimensional view of the two-pronged cervical staple impactor 900. It has a handle 901, a stem 902, and a screw insert 903 which can be screwed into the threaded staple insert. The impactor has two wings 904 which keep the staple base edges in place facilitating staple impaction. The handle 901 of the impactor 900 is broad in order to allow impaction by a mallet.

FIGS. 10A-C illustrate three-dimensional views of the four-pronged cervical staple impactor 1000 (Embodiment II). It has the same features as the two-pronged impactor 900, except its wings 1004 are broader accommodating the broader staple base. The impactor 1000 also includes a handle 1001, a stem 1002, and an impact screw 1003.

FIG. 11A illustrates a three-dimensional view of placement of the two pronged cervical facet staple 700 into a cervical spine model having vertebral body 1103 and lamina 1104. One staple 700 is perched on the joint 1101 prior to impaction. The other staple 700 is impacted.

FIG. 11B illustrates a three-dimensional view of placement of the four pronged cervical facet staple 800 into a cervical spine pre and post impaction.

FIG. 11C illustrates the concept of modularity and incremental diminution of movement of the joint by the modular placement of different combinations and permutations of varying numbers of two and four pronged cervical facet staples 700, 800. If one wishes to have the most flexible (least rigid) fusion, one would place a unilateral two pronged staple 700. One can increase i.e. calibrate increasing degrees of rigidity by increasing the number of prongs penetrating the facet joints bilaterally. In FIG. 11C each facet joint is fused using a total number of six prongs. One side this is accomplished by using three two pronged staples 700, and on the other side using one four pronged staple 800 and one two pronged staple 700. These two embodiments can be mixed and matched unilaterally or bilaterally to vary the degree of rigidity and conversely flexibility of fusion. The most flexible fusion at one level would be accomplished by one staple 700 (2 prongs). The highest level of rigidity would be achieved by placing two four pronged staples 800 on both sides totaling sixteen prongs. Intermediate degrees of relative joint motion can be modulated by insertion into the cervical facet joints staples in two-four prong increments from 2-16. Each additional prong further limits the degree of facet joint motion hence increasing rigidity, and conversely decreasing flexibility. Thus the novel modular use of these embodiments heralds an era of flexible cervical spine fusion.

FIGS. 12 A-B illustrate a lumbar facet joint staple 1200 in open and closed positions and having staple prongs 1203. This lumbar facet staple has been thoroughly described in our previous co-pending patent application Ser. No. 11/536,815, filed on Sep. 29, 2006, and Ser. No. 11/208,644, filed on Aug. 23, 2005, the relevant portion of each of which is hereby incorporated by reference hereinafter. The new improvement of this device includes a ratchet 1201. The staple 1200 can be incrementally closed with increased ratcheting over increasing number of spurs 1202. This achieves increasing calibrated levels of lumbar facet joint fusion, and conversely diminishing joint flexibility. This new designs further enhances the capacity to achieve flexible fusions in the lumbar spine.

2. The Surgical Method

Exemplary surgical steps for practicing one or more of the foregoing embodiments will now be described.

The posterior lumbar spine implantation of all the screw box 100, 200, 300 embodiments, with BDFT screws, and horizontal mini-plate 400 can be implanted via previously described posterior lumbar interbody fusion (PLIF) or posterior transforaminal lumbar interbody fusion (TLIF) procedures. The procedures can be performed open, microscopic, closed tubular or endoscopic. Fluoroscopic guidance can be used with any of these procedures.

After adequate induction of anesthesia, the patient is placed in the prone position. A midline incision is made for a PLIF procedure, and one or two parallel paramedian incisions or a midline incision is made for the TLIF procedure. For the PLIF, a unilateral or bilateral facet sparing hemi-laminotomy is created to introduce screw box 100, 200, 300 embodiments I-III into the disc space, after it is adequately prepared.

For the TLIF procedure, after unilateral or bilateral dissection and drilling of the inferior articulating surface and the medial superior articulating facet the far lateral disc space is entered and a circumferential discectomy is performed. The disc space is prepared and the endplates exposed.

Then one screw box 100, 200, 300 of either embodiments I-III is placed on either right, left or both sides. Then another screw box of embodiments 100, 200, 300 I-III is placed on the contralateral side. For embodiment I the external screw guide 505/box expander is attached to the screw box (FIGS. 5A-H). First the Allen key 501 is screwed until the box conforms perfectly to the height and depth of the space. Then a pilot hole can be drilled or an awl can start a pilot hole in the vertebral bodies. Then a transvertebral screw is screwed into the vertebral body via the built-in box screw guides 505. For difficult angles, an angled screw driver can be employed.

For embodiments II-III the same method is used for placing screws, except the Allen key 501 is not utilized in the absence of plate expansion.

If bilateral constructs have been inserted, bone is packed into the intervertebral space, as well as within the device. Then the horizontal intervertebral zero profile mini-plate 400 is slid beneath the thecal sac and is secured to both left and right screw boxes with small mini-plate screws 210 (FIGS. 4A-B). This prevents bone intrusion into the thecal sac and hence possible nerve root compression.

FIGS. 6A and B illustrate the process of insertion and final placement of the construct into the lumbar spine. The mini-plates 400 can come in different horizontal lengths and widths to accommodate different intra and inter-patient disc space diameters. The BDFT screws can come in different widths, lengths and thread designs.

The anterior thoracic and lumbar spine implantation of one, two or three screw box constructs 100, 200, 300 and BDFT screws can be performed in a similar manner to the posterior application. Likewise, a horizontal mini-plate 400 can be used to cap two or three screw box constructs 100, 200, 300 (one placed midline deeply, one placed left and one placed right, forming a triangulation). Alternatively two screw box constructs may be placed into a circumferential ring for anterior placement. Anterior placement of these devices can be performed into the L4/5 and L5/S1 spaces on the supine anesthetized patient via previously described open microscopic or endoscopic techniques. Once the disc space is exposed and discectomy and space preparation are performed, placement of one, two or three screw box embodiments 100, 200, 300 (I-III) or a 2 in I construct can be placed. The screw placement is facilitated by the internal screw guides, and different positioning tools ((FIG. 5). A right angled screw driver and/or ratchet could alternatively be employed A capping mini-plate 400 may be applied if desirable. The mechanism of screw placement and mini-plate 400 attachment are identical to what was described above.

The posterior placement of screw box constructs 100, 200, 300 alone or combined with horizontal mini-plates 400 into the thoracic spine can be performed via previously described transpedicular approaches; open or endoscopic. The anterior placement into the thoracic spine can be accomplished via a trans-thoracic approach. Once the disc space is exposed via either approach, any combination of the above mention Embodiments (I-III) can be inserted. Engagement of the devices is identical to what was mentioned above.

For posterior placement of cervical facet staple 700, 800 embodiments, after adequate induction of anesthesia the patient is flipped prone and his head and neck secured. A single midline or two para-median incisions are made for unilateral or bilateral or multilevel placement of staples. Ultimately the facet joint is exposed. Alternatively and preferably this can be performed percutaneously under fluoroscopic guidance with intravenous sedation. The staple 700, 800 (Embodiments I or II) is loaded into the impactor 900, 1000. The staple 700, 800 is placed on the two articulating cervical facets, and then impacted into the joint. To achieve modular calibrated fusion different combinations and permutations of cervical facet stales can be inserted ranging from a single unilateral two pronged staple providing a high degree of flexibility to a total of four bilaterally placed four pronged staples 800 (16 prongs) leading to the highest degree of rigidity. Additional bone may or may not be placed in its vicinity to facilitate permanent and solid fusion. This procedure can be performed open, closed, percutaneously, tubulary, endoscopically or microscopically. FIGS. 11A-C illustrates placement of the staples 700, 800 in the cervical spine.

We have previously described surgical placement of the lumbar facet joint staple in our two co-pending patents. The surgical procedure for this device is identical to that which has been previously mentioned.

The present inventions may provide effective and safe techniques that overcome the problems associated with current transpedicular based cervical, thoracic and lumbar fusion technology, and for many degenerative stable and unstable spine disease. These inventions could replace much pedicle screw-based instrumentation in many but not all degenerative spine conditions.

The speed and simplicity of placement of cervical and lumbar facet staples, and placement of Lumbar screw box-BDFT constructs far exceeds that of current pedicle screw technology. Furthermore, these devices have markedly significantly decreased risk of misguided screw placement, and hence decreased risk of neural and vascular injury, and blood loss. In the lumbar spine BDFT screw constructs and facet staples could be applied modularly in different combinations to achieve different degrees of rigidity (flexibility). Patients having these devices would have decreased recovery and back to work time. These devices most likely lead to similar if not equal fusion with significantly less morbidity, and hence overall make them a major advance in the evolution of spinal instrumented technology leading to advances in the care of the spinal patient.

Another major novelty and advance is the introduction of simple and safe modular calibrated cervical flexible fusion. To our knowledge neither a similar device nor a similar mathematical concept of modular joint flexibility/fusion calibration has been postulated for the cervical spine or for any other articulating joint.

To our knowledge there have not been any previously described similar posterior lumbar and thoracic combined spacer and screw constructs. These devices can similarly be modified to stabilize bone fractures throughout the entire body. To our knowledge the description of zero to subzero profile anterior or posterior horizontal spinal plates which traverse the diameter of the disc space has not been previously described.

We claim:

1. A tool for manipulating and inserting a universal, intervertebral bone fusion spacer into a disc space between a first vertebral body and a second vertebral body for providing fusion of the first vertebral body to the second vertebral body via biological bone fusion and screw fusion, wherein the universal, intervertebral bone fusion spacer includes an intervertebral cage having a first integral screw guide and a second integral screw guide, wherein each longitudinal end of the intervertebral cage includes a slot or indentation formed adjacent to an edge of an upper surface of the intervertebral cage, the tool comprising:

a gripper having a plurality of prongs,
wherein a distal end of each of the plurality of prongs is capable of engaging a respective slot or indentation of the intervertebral cage; and a screw guide for controlling a direction of screws that are inserted into the first integral screw guide and the second integral screw guide,
wherein the screw guide is positioned between the plurality of prongs.

2. The tool of claim 1, further comprising:
wherein the plurality of prongs engage and hold the screw guide in place.

3. The tool of claim 1, wherein the screw guide includes a slot or indentation for receiving one of the plurality of prongs.

4. The tool of claim 1, wherein the screw guide includes slots or indentations on opposing sides for receiving the plurality of prongs.

5. The tool of claim 1, wherein the screw guide includes an integral trajectory guide that is capable of receiving and guiding one of the screws of the universal, intervertebral bone fusion spacer.

6. The tool of claim 1, further comprising a handle wherein the gripper includes a tubular portion that is capable of receiving and guiding a portion of the handle therein.

7. The tool of claim 1, further comprising a handle, wherein an end of the handle includes a rectangular handle portion.

8. The tool of claim 1, further comprising a handle, wherein an end of the handle includes a circular handle portion.

9. The tool of claim 1, further comprising:
a driver assembly, the driver assembly including:
a driver handle;
a drive bit portion; and
a flexible drive shaft extending between the driver handle and the drive bit portion for manipulating one of the screws of the universal, intervertebral bone fusion spacer.

10. The tool of claim 1, wherein the intervertebral cage includes a wall having an entry opening of the first integral screw guide and an entry opening of the second integral screw guide,
wherein the wall has four quadrants delineated by a first axis and a second axis each lying in a plane of the wall, and the first axis is at a right angle with respect to the second axis,
wherein the four quadrants include a first quadrant, a second quadrant, a third quadrant, and a fourth quadrant,
wherein the first quadrant and the fourth quadrant are opposed to the second quadrant and the third quadrant with respect to the first axis, and the first quadrant and the second quadrant are opposed to the third quadrant and the fourth quadrant with respect to the second axis,
wherein the first quadrant is diagonally opposed to the third quadrant, and the second quadrant is diagonally opposed to the fourth quadrant, and
wherein one of:
a majority of an area of the entry opening of the first integral screw guide is in the first quadrant and a majority of an area of the entry opening of the second integral screw guide is in the third quadrant; and
the majority of the area of the entry opening of the first integral screw guide is in the second quadrant and the majority of the area of the entry opening of the second integral screw guide is in the fourth quadrant.

11. The tool of claim 1, wherein the intervertebral cage includes a wall having an entry opening of the first integral screw guide and an entry opening of the second integral screw guide,
wherein the wall has four quadrants delineated by a first axis and a second axis each lying in a plane of the wall, and the first axis is at a right angle with respect to the second axis,
wherein the four quadrants include a first quadrant, a second quadrant, a third quadrant, and a fourth quadrant,
wherein the first quadrant and the fourth quadrant are opposed to the second quadrant and the third quadrant with respect to the first axis, and the first quadrant and the second quadrant are opposed to the third quadrant and the fourth quadrant with respect to the second axis,
wherein the first quadrant is diagonally opposed to the third quadrant, and the second quadrant is diagonally opposed to the fourth quadrant, and wherein one of:
a center of the entry opening of the first integral screw guide is in the first quadrant and a center of the entry opening of the second integral screw guide is in the third quadrant; and
the center of the entry opening of the first integral screw guide is in the second quadrant and the center of the entry opening of the second integral screw guide is in the fourth quadrant.

12. The tool of claim 1, wherein the intervertebral cage includes a wall having an entry opening of the first integral screw guide and an entry opening of the second integral screw guide, the wall including a first corner and a second corner, the first corner being arranged at an opposite side of the wall and an opposite end of the wall with respect to the second corner,
wherein the first integral screw guide and the second integral screw guide are diagonally arranged along a direction extending from the first corner of the wall to the second corner of the wall.

13. The tool of claim 1, wherein the intervertebral cage includes a wall having an entry opening of the first integral screw guide and an entry opening of the second integral screw guide, the wall including a first corner and a second corner, the first corner being arranged at an opposite side of the wall and an opposite end of the wall with respect to the second corner,
wherein the first integral screw guide and the second integral screw guide are adjacent to each other along a longitudinal extent of the wall and are diagonally arranged along a direction extending from the first corner of the wall to the second corner of the wall.

14. The tool of claim 1, wherein the intervertebral cage includes an arcuate wall.

15. A tool assembly comprising:
a universal, intervertebral bone fusion spacer for insertion into a disc space between a first vertebral body and a second vertebral body and fusion of the first vertebral body to the second vertebral body via biological bone fusion and screw fusion, the universal, intervertebral bone fusion spacer comprising:
an intervertebral cage including a first integral screw guide and a second integral screw guide; and
a first screw disposed in the first integral screw guide and at least partially within the intervertebral cage;
a second screw disposed in the second integral screw guide and at least partially within the intervertebral cage,
wherein a surface of each longitudinal end of the intervertebral cage includes a slot or indentation formed adjacent to an edge of an upper surface of the intervertebral cage for receiving a distal end of a prong of an implantation tool; and
a tool for manipulating and inserting the universal, intervertebral bone fusion spacer into the disc space between the first vertebral body and the second vertebral body to provide fusion of the first vertebral body to the second vertebral body via biological bone fusion and screw fusion, the tool comprising:
a gripper having a plurality of prongs,
wherein a distal end of each of the plurality of prongs engages a respective slot or indentation of the intervertebral cage; and
a screw guide for controlling a direction of the first screw and the second screw that are inserted into the first integral screw guide and the second integral screw guide,
wherein the screw guide is positioned between the plurality of prongs.

16. The tool assembly of claim 15, wherein the plurality of prongs engage and hold the screw guide in place.

17. The tool assembly of claim 15, wherein the screw guide includes a slot or indentation for receiving one of the plurality of prongs.

18. The tool assembly of claim 15, wherein the screw guide includes slots or indentations on opposing sides for receiving the plurality of prongs.

19. The tool assembly of claim 15, wherein the screw guide includes an integral trajectory guide that is capable of receiving and guiding one of the first screw and the second screw of the universal, intervertebral bone fusion spacer.

20. The tool assembly of claim 15, further comprising a handle, wherein the gripper includes a tubular portion that is capable of receiving and guiding a portion of the handle therein.

21. The tool assembly of claim 15, further comprising a handle, wherein an end of the handle includes a rectangular handle portion.

22. The tool assembly of claim 15, further comprising a handle, wherein an end of the handle includes a circular handle portion.

23. The tool assembly of claim 15, further comprising:
a driver assembly, the driver assembly including:
a driver handle;
a drive bit portion; and
a flexible drive shaft extending between the driver handle and the drive bit portion and manipulating one of the first screw and the second screw of the universal, intervertebral bone fusion spacer.

24. The tool assembly of claim 15, wherein each of the first internal screw guide and the second internal screw guide is angled to orient the first screw and the second screw bi-directionally in opposite directions.

25. The tool assembly of claim 15, wherein the first screw is a self-tapping and self-drilling screw having a tapered end and a threaded body, and
wherein the second screw is a self-tapping and self-drilling screw having a tapered end and a threaded body.

26. The tool assembly of claim 15, further comprising:
a bone graft cavity for receiving bone packing material for bone fusion between the first vertebral body and the second vertebral body.

27. The tool assembly of claim 15, wherein the intervertebral cage includes a side having a plurality of ridges.

28. The tool assembly of claim 15, wherein the first integral screw guide and the second integral screw guide are adjacent to each other and at an angulation with respect to a wall having the first integral screw guide and the second integral screw guide.

29. The tool assembly of claim 28, wherein a first angulation of the first integral screw guide is opposed to a second angulation of the second integral screw guide.

30. The tool assembly of claim 15, wherein the first integral screw guide and the second integral screw guide are adjacent to each other along a longitudinal extent of a wall having the first integral screw guide and the second integral screw guide, and
wherein the first integral screw guide and the second integral screw guide are offset in opposite directions with respect to a center line of the longitudinal extent.

31. The tool assembly of claim 30, wherein a part of the first integral screw guide overlaps a part of the second integral screw guide along the longitudinal extent of the wall having the first integral screw guide and the second integral screw guide.

32. The tool assembly of claim 30, wherein the first integral screw guide and the second integral screw guide are at an angulation with respect to the wall having the first integral screw guide and the second integral screw guide.

33. The tool assembly of claim 32, wherein a first angulation of the first integral screw guide extends in a first direction from the wall having the first integral screw guide and the second integral screw guide toward a first side of the intervertebral cage,
wherein a second angulation of the second integral screw guide extends in a second direction from the wall having the first integral screw guide and the second integral screw guide toward a second side of the intervertebral cage, and
wherein the first side is opposed to the second side.

34. The tool assembly of claim 15, wherein the first integral screw guide and the second integral screw guide are at an angulation with respect to a wall having the first integral screw guide and the second integral screw guide.

35. The tool assembly of claim 15, wherein the first integral screw guide and the second integral screw guide diverge from each other.

36. The tool assembly of claim 15, wherein the first integral screw guide and the second integral screw guide diverge from each other and at an angulation with respect to a wall having the first integral screw guide and the second integral screw guide.

37. The tool assembly of claim 26, wherein the bone graft cavity is accessible through an opening formed in a lateral wall of the intervertebral cage, a perimeter of the opening including an indentation through which one of the first screw and the second screw passes from the bone graft cavity to an exterior of the intervertebral cage.

38. A method of inserting a universal, intervertebral bone fusion spacer into a disc space between a first vertebral body and a second vertebral body using a tool for manipulating and inserting the universal, intervertebral bone fusion spacer into the disc space between the first vertebral body and the second vertebral body,
wherein the universal, intervertebral bone fusion spacer includes:
an intervertebral cage having a first integral screw guide and a second integral screw guide, wherein a surface of each longitudinal end of the intervertebral cage includes a slot or indentation formed adjacent to an edge of an upper surface of the intervertebral cage for receiving a distal end of a prong of tool; and
wherein the tool includes:
a gripper having a plurality of prongs,
wherein a distal end of each of the plurality of prongs is capable of engaging a respective slot or indentation of the intervertebral cage, and
a screw guide for controlling a direction of a first screw and a second screw that are inserted into the first integral screw guide and the second integral screw guide, wherein the screw guide is positioned between the plurality of prongs, and the method comprising:

measuring a dimension of the disc space between the first vertebral body and the second vertebral body;

determining that the disc space is a lateral disc space, an anterior lateral disc space, a posterior lumbar disc space, an anterior lumbar disc space, or an anterior cervical disc space;

selecting the universal, intervertebral bone fusion spacer based on the measured dimension of the disc space and based on the determination of the disc space being the lateral disc space, the anterior lateral disc space, the posterior lumbar disc space, or the anterior cervical disc space;

selecting the screw guide based on the selected universal, intervertebral bone fusion spacer and positioning the screw guide between the plurality of prongs;

positioning the intervertebral cage between the plurality of prongs such that each slot or indentation of the intervertebral cage corresponds with the distal end of each of the plurality of prongs;

inserting the selected universal, intervertebral bone fusion spacer into a midline of the disc space using the tool until the selected universal, intervertebral bone fusion spacer is flush or countersunk relative to the first vertebral body and the second vertebral body; and confirming a position and placement of the universal, intervertebral bone fusion spacer relative to the first vertebral body and the second vertebral body.

39. A method of inserting a universal, intervertebral bone fusion spacer into a disc space between a first vertebral body and a second vertebral body and fusing the first vertebral body to the second vertebral body via biological bone fusion and screw fusion using a tool for manipulating and inserting the universal, intervertebral bone fusion spacer into the disc space between the first vertebral body and the second vertebral body, wherein the universal, intervertebral bone fusion spacer includes:
an intervertebral cage including:
a first integral screw guide;
a second integral screw guide; and
a first screw disposed in the first integral screw guide and at least partially within the intervertebral cage;
a second screw disposed in the second integral screw guide and at least partially within the intervertebral cage,
wherein a surface of each longitudinal end of the intervertebral cage includes a slot or indentation formed adjacent to an edge of an upper surface of the intervertebral cage for receiving a distal end of a prong of an implantation tool; and
wherein the tool includes:
a gripper having a plurality of prongs,
wherein a distal end of each of the plurality of prongs is capable of engaging engages a respective slot or indentation of the intervertebral cage, and
a screw guide for controlling a direction of the first screw and the second screw that are inserted into the first integral screw guide and the second integral screw guide, wherein the screw guide is positioned between the plurality of prongs, and the method comprising:

measuring a dimension of the disc space between the first vertebral body and the second vertebral body;

determining that the disc space is a lateral disc space, an anterior lateral disc space, a posterior lumbar disc space, an anterior-lateral lumbar disc space, an anterior lumbar disc space, or an anterior cervical disc space;

selecting the universal, intervertebral bone fusion spacer based on the measured dimension of the disc space and based on the determination of the disc space being the lateral disc space, the anterior lateral disc space, the posterior lumbar disc space, the anterior-lateral lumbar disc space, the anterior lumbar disc space, or the anterior cervical disc space;

engaging each slot or indentation of the intervertebral cage with the distal end of each of the plurality of prongs;

inserting the selected universal, intervertebral bone fusion spacer into a midline of the disc space using the tool until the selected universal, intervertebral bone fusion spacer is flush or countersunk relative to the first vertebral body and the second vertebral body;

inserting the first screw into the first internal screw guide of the selected universal, intervertebral bone fusion spacer;

inserting the second screw into the second internal screw guide of the selected universal, intervertebral bone fusion spacer;

screwing the first screw and the second screw into the first vertebral body and the second vertebral body respectively;

confirming a position and placement of the universal, intervertebral bone fusion spacer relative to the first vertebral body and the second vertebral body.

40. A tool assembly comprising:

a universal, intervertebral bone fusion spacer for insertion into a disc space between a first vertebral body and a second vertebral body and fusion of the first vertebral body to the second vertebral body via biological bone fusion and screw fusion, the universal, intervertebral bone fusion spacer comprising:
an intervertebral cage including:
a first integral screw guide;
a second integral screw guide; and
a bone graft cavity for receiving bone packing material for bone fusion between the first vertebral body and the second vertebral body;
a first screw disposed in the first integral screw guide and at least partially within the intervertebral cage;
a second screw disposed in the second integral screw guide and at least partially within the intervertebral cage,
wherein the bone graft cavity extends through the intervertebral cage for receiving bone packing material for bone fusion between the first vertebral body and the second vertebral body and across the intervertebral space,
wherein each of the first internal screw guide and the second internal screw guide is angled to orient the first screw member and the second screw bi-directionally in opposite directions,
wherein each of the first internal screw guide and the second internal screw guide includes a tunnel that permits only a predetermined angled trajectory of the first screw and the second screw, and a predetermined angled trajectory of the first internal screw guide is different than a predetermined angled trajectory of the second internal screw guide,
wherein the intervertebral cage includes an exit for one of the first integral screw guide and the second integral screw guide, the exit being adjacent to or formed in an edge of the bone graft cavity, wherein the first screw is a self-tapping and self-drilling screw having a tapered end and a threaded body, and wherein the second screw is a self-tapping and self-drilling screw having a tapered end and a threaded body, wherein the intervertebral cage includes a side having a plurality of ridges, wherein a surface of each longitudinal end of the intervertebral cage includes a slot or indentation formed adjacent to an edge of an upper surface of the intervertebral cage for receiving a distal end of a prong of an implantation tool, wherein the intervertebral cage includes a wall having an entry opening of the first integral screw guide and an entry opening of the second integral screw guide, wherein the wall has four quadrants delineated by a first axis and a second axis each lying in a plane of the wall, and the first axis is at a right angle with respect to the second axis, wherein the four quadrants include a first quadrant, a second quadrant, a third quadrant, and a fourth quadrant, wherein the first quadrant and the fourth quadrant are opposed to the second quadrant and the third quadrant with respect to the first axis, and the first quadrant and the second quadrant are opposed to the third quadrant and the fourth quadrant with respect to the second axis, wherein the first quadrant is diagonally opposed to the third quadrant, and the second quadrant is diagonally opposed to the fourth quadrant, and wherein one of:
a majority of an area of the entry opening of the first integral screw guide is in the first quadrant and a majority of an area of the entry opening of the second integral screw guide is in the third quadrant; and
the majority of the area of the entry opening of the first integral screw guide is in the second quadrant and the majority of the area of the entry opening of the second integral screw guide is in the fourth quadrant; and a tool for manipulating and inserting the universal, intervertebral bone fusion spacer into the disc space between the first vertebral body and the second vertebral body to provide fusion of the first vertebral body to the second vertebral body via biological bone fusion and screw fusion, the tool comprising:
a gripper having a plurality of prongs,
wherein a distal end of each of the plurality of prongs engages a respective slot or indentation of the intervertebral cage; and
a screw guide for controlling a direction of the first screw and the second screw that are inserted into the first integral screw guide and the second integral screw guide,
wherein the screw guide is positioned between the plurality of prongs, and
wherein the screw guide includes slots or indentations on opposing sides for receiving the plurality of prongs.

41. A tool assembly comprising:
a universal, intervertebral bone fusion spacer for insertion into a disc space between a first vertebral body and a second vertebral body for fusion of the first vertebral body to the second vertebral body via biological bone fusion and screw fusion, the universal, intervertebral bone fusion spacer comprising:
an intervertebral cage including:
a plurality of internalized screw guides, wherein each of the plurality of internalized screw guides includes a proximal screw head recess that is entirely encased within an upper surface of the intervertebral cage, wherein each of the plurality of internalized screw guides includes a tunnel-guide that projects into the intervertebral cage from the proximal screw head recess, the tunnel-guide including a proximal tunnel-guide portion that is entirely encased by walls of the intervertebral cage and a distal tunnel-guide portion that is partially encased by the walls of the intervertebral cage, the distal tunnel-guide portion being contiguous with and exiting into a bone cavity of superior and inferior walls of the intervertebral cage, and wherein a surface of each longitudinal wall of the intervertebral cage includes a slot or indentation formed adjacent to an edge of the upper surface of the intervertebral cage; and
a screw disposed in each of the plurality of internalized screw guides and at least partially within the intervertebral cage; and
a tool for manipulating and inserting the universal, intervertebral bone fusion spacer into the disc space between the first vertebral body and the second vertebral body for providing fusion of the first vertebral body to the second vertebral body via biological bone fusion and screw fusion, the tool comprising:
a gripper having a plurality of prongs each having a distal end,
wherein the distal end of each of the plurality of prongs respectively is capable of engaging the slot or indentation of the intervertebral cage on the surface of each longitudinal wall of the intervertebral cage; and
a screw guide for controlling a direction of the first screw and the second screw that are inserted into the first integral screw guide and the second integral screw guide,
wherein the screw guide is positioned between the plurality of prongs, and
wherein the screw guide includes slots or indentations on opposing sides for receiving the plurality of prongs.

42. The tool assembly of claim 41, wherein the distal tunnel-guide portion that is partially encased by the walls of the intervertebral cage is parabola shaped.

43. The tool assembly of claim 42, wherein the screw extends through one of the plurality of internalized screw guides via the proximal screw head recess that is entirely encased within a top plane of the intervertebral cage, into the proximal tunnel-guide portion that is entirely encased by the walls of the intervertebral cage, into the parabola shaped distal tunnel-guide portion that is partially encased by the walls of the intervertebral cage, and then exits from the bone cavity of the superior and inferior walls.

44. The tool assembly of claim 41, wherein the bone cavity is accessible through an opening formed in a lateral wall of the intervertebral cage, a perimeter of the opening including an indentation through which the screw passes from the bone cavity to an exterior of the intervertebral cage.

* * * * *